United States Patent
Fontayne et al.

(10) Patent No.: US 6,554,759 B2
(45) Date of Patent: Apr. 29, 2003

(54) TARGETING FIXTURE

(75) Inventors: Diego Y. Fontayne, Montebello, NY (US); Scott D. Salmon, Hoboken, NJ (US)

(73) Assignee: Integrated Implant Systems LLC, Arlington, VA (US)

( * ) Notice: Subject to any disclaimer, the term of this patent is extended or adjusted under 35 U.S.C. 154(b) by 0 days.

(21) Appl. No.: 09/858,657

(22) Filed: May 17, 2001

(65) Prior Publication Data

US 2002/0007103 A1 Jan. 17, 2002

Related U.S. Application Data

(60) Provisional application No. 60/205,094, filed on May 18, 2000.

(51) Int. Cl.$^7$ .............................................. A61M 36/00
(52) U.S. Cl. ................................. 600/7; 606/7; 600/459
(58) Field of Search .............................. 600/1, 2, 7, 8, 600/459, 462, 463, 464; 606/1, 130; 128/920, 922

(56) References Cited

U.S. PATENT DOCUMENTS

| | | | |
|---|---|---|---|
| 5,871,448 A | | 2/1999 | Ellard .......................... 600/459 |
| 5,931,786 A | * | 8/1999 | Whitmore et al. .......... 600/459 |
| 5,938,583 A | | 8/1999 | Grimm .......................... 600/7 |
| 6,129,670 A | * | 10/2000 | Burdette et al. ............ 600/427 |
| 6,387,034 B1 | * | 5/2002 | Lee ................................ 600/1 |

FOREIGN PATENT DOCUMENTS

| | | |
|---|---|---|
| WO | 97/22379 | 6/1997 |

* cited by examiner

Primary Examiner—Teresa Walberg
Assistant Examiner—Thor Campbell
(74) Attorney, Agent, or Firm—Heller Ehrman White & McAuliffe LLC

(57) ABSTRACT

A targeting fixture allows for x-y-z movement of a targeting fixture with respect to a grid template. The targeting fixture includes a sheath unit, which accepts a seed implanting device. The sheath unit is maintained at a fixed relation with respect to the grid template.

3 Claims, 26 Drawing Sheets

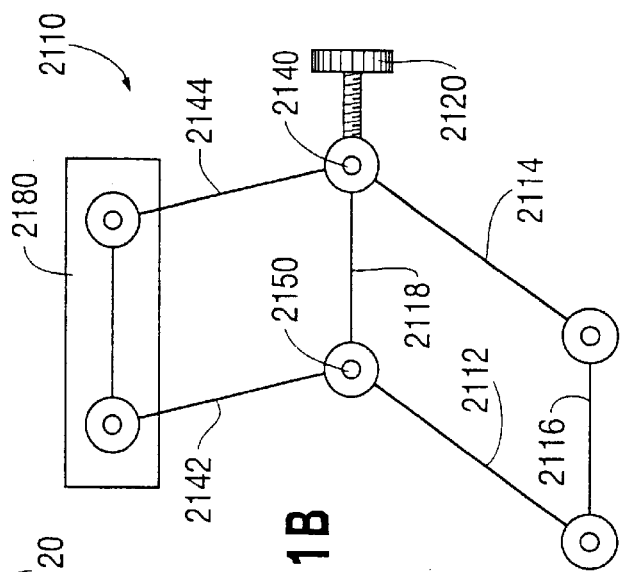
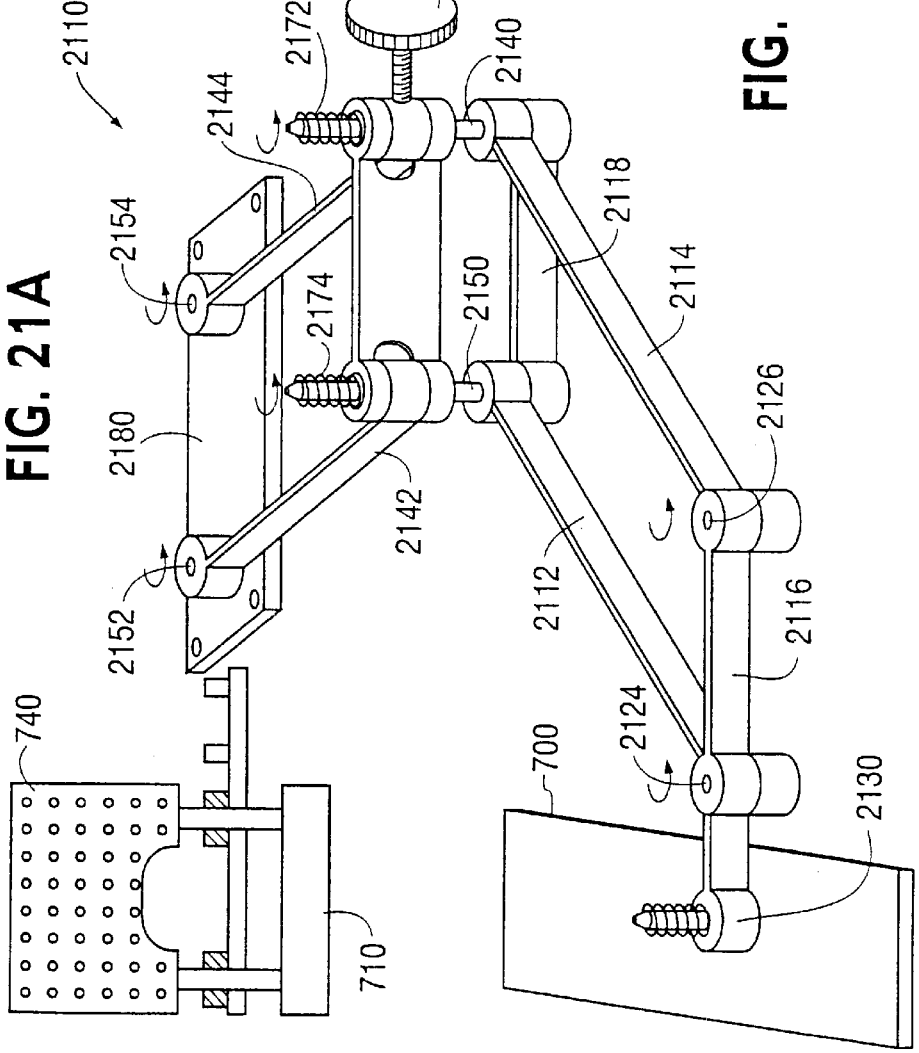
FIG. 21A
FIG. 21B

TARGETING FIXTURE

This application claims the benfit of No. 60/205,094, filed May 18, 2000.

BACKGROUND OF THE INVENTION

1. Field of the Invention

The present invention relates to a targeting fixture that provides for three degrees of freedom with respect to a grid template. More particularly, the present invention relates to a targeting fixture for providing a seed-implanting instrument in a particular x,y,z location with respect to a grid template, to thereby apply the seeds in order to treat a patient.

2. Description of the Related Art

For treating prostate cancer, radioactive seeds are provided to various locations within a patient's prostate gland. Typically, a base unit which includes an ultrasound unit is used to determine the exact location of the patient's prostate gland with respect to the base unit. The ultrasound unit includes a probe, which is inserted into the patient's rectum while the patient is lying on his back. A grid template is mounted onto a stepper unit that is itself mounted onto an angular adjustment unit (or "base unit"), whereby the grid template includes a plurality of rows and columns of holes in which a needle can be inserted. Typically, the grid template includes 13 by 13 matrix of needle holes, where adjacent holes on a row or column are 5 mm apart. Every other row is labeled with a number, and every other column is labeled with an alphabetic character. There is a direct relation between the centerline axis of the ultrasound probe and the position of the holes of the grid template. The base unit/stepper unit structure is capable of moving either in a radial direction or in an inwards or outwards direction with respect to the patient.

By using the ultrasound unit, a precise position of the proximal and distal positions of the prostate gland can be determined and recorded. The distal position of the prostate gland is also called the "zero retraction point". Once that information is recorded, a pre-plan can be determined by a doctor, where the pre-plan corresponds to a plan for injecting seeds into particular locations within the patient's prostate gland. Such treatment is generally started by placing the needle at the zero retraction point, and then applying seeds with respect to that reference point. After the pre-plan has been determined, a needle is provided through a hole on the grid template, and then inserted into a region within the patient's body in which the prostate gland is located.

For a conventional seed implantation device, a needle is first placed into a particular hole of the grid template, and then the seed implantation device is held in place by a doctor and attached to the needle. The seed implantation device is then used to inject one or more seeds into the patient's body through the needle. When finished with that hole, the seed implantation device is deattached from the needle, and placed aside. Then, the needle is removed from the grid template, and a new needle is positioned at another hole of the grid template, according to the specific pre-plan for treating the patient's prostate gland. One such conventional seed implantation device is called a MICK applicator, and requires the operator to physically reposition the MICK applicator back onto a new needle positioned onto the grid template.

With such a scheme, the instrument may become unsterile when it is placed aside between replacements of needles. Also, there may exist inaccuracies due to the doctor not placing the instrument at the correct seed-implanting position with respect to the grid template (z-axis position) due to the instrument being somewhat unwieldy and hard to hold in place.

SUMMARY OF THE INVENTION

One object of the present invention is to provide a mounting device that mounts to a mounting structure on which a grid template is also mounted, and that allows a seed-implanting instrument to be accurately placed into a proper x,y,z location with respect to the grid template, for implanting seeds into a patient's body.

Another object of the present invention is to provide a mounting device for a grid template that properly positions an instrument so that it is lined up orthogonally with respect to a front face of the grid template, no matter what x,y,z position the mounting device is currently positioned.

BRIEF DESCRIPTION OF THE DRAWINGS

The invention will become more fully apparent from the following detailed description when read in conjunction with the accompanying drawings with like reference numerals indicating corresponding parts throughout, and wherein:

FIGS. 21A and 21B show a targeting fixture according to an eighth embodiment of the invention;

DETAILED DESCRIPTION OF THE PREFERRED EMBODIMENTS

Figure 1:
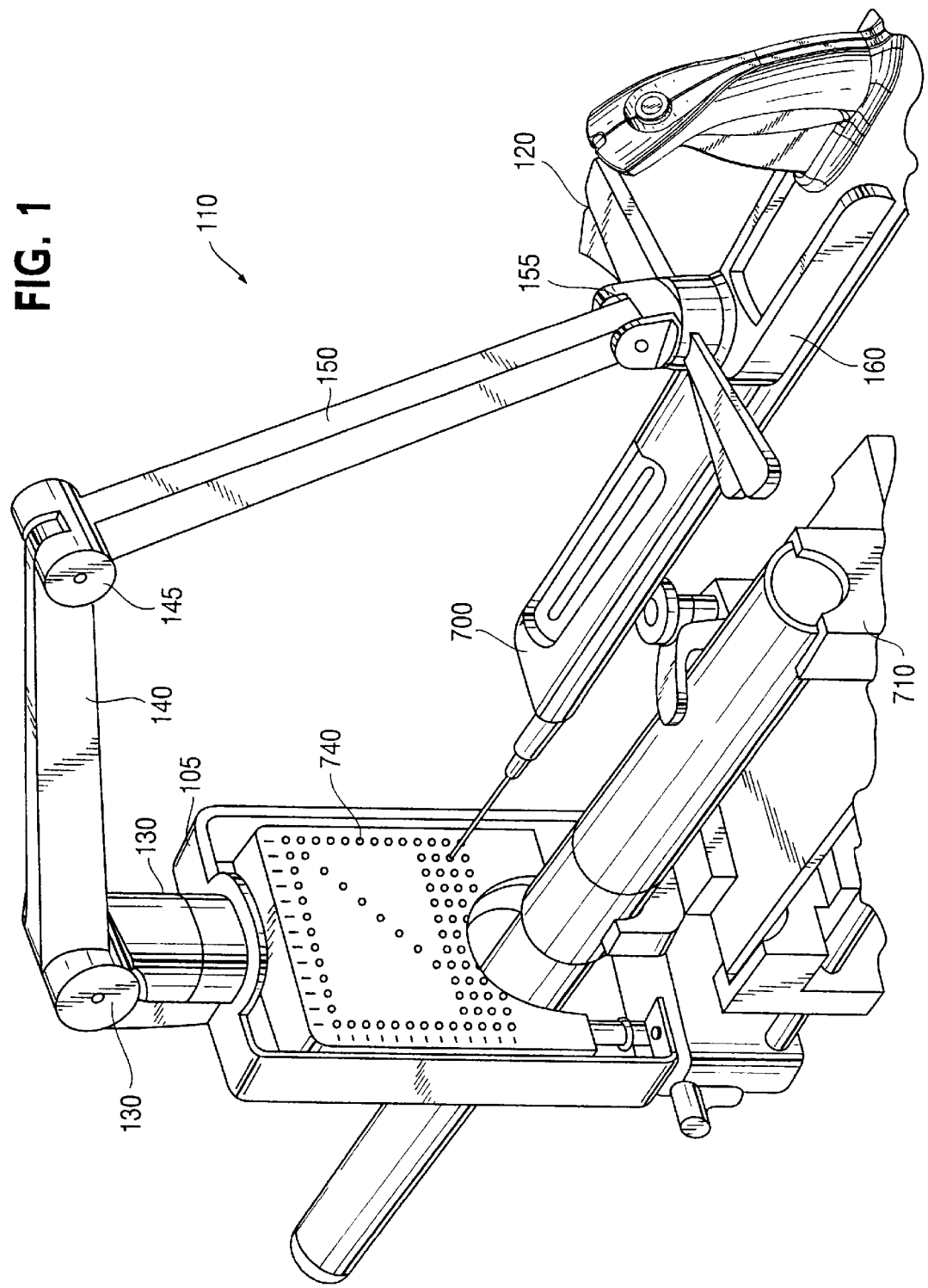
FIG. 1 shows a targeting fixture according to a second embodiment of the invention.

Preferred embodiments of the present invention will be described in detail hereinbelow, with reference to the drawings. In the drawings, preferred dimensions, in inches, are provided by way of explanation of the present invention and not by way of limitation. In other words, the present invention is directed to a particular method and apparatus and equivalents thereof with respect to a targeting fixture for attaching to a device on which a grid template is also attached to, and not to the exact sizes of the elements that make up the targeting fixture.

Figure 7:
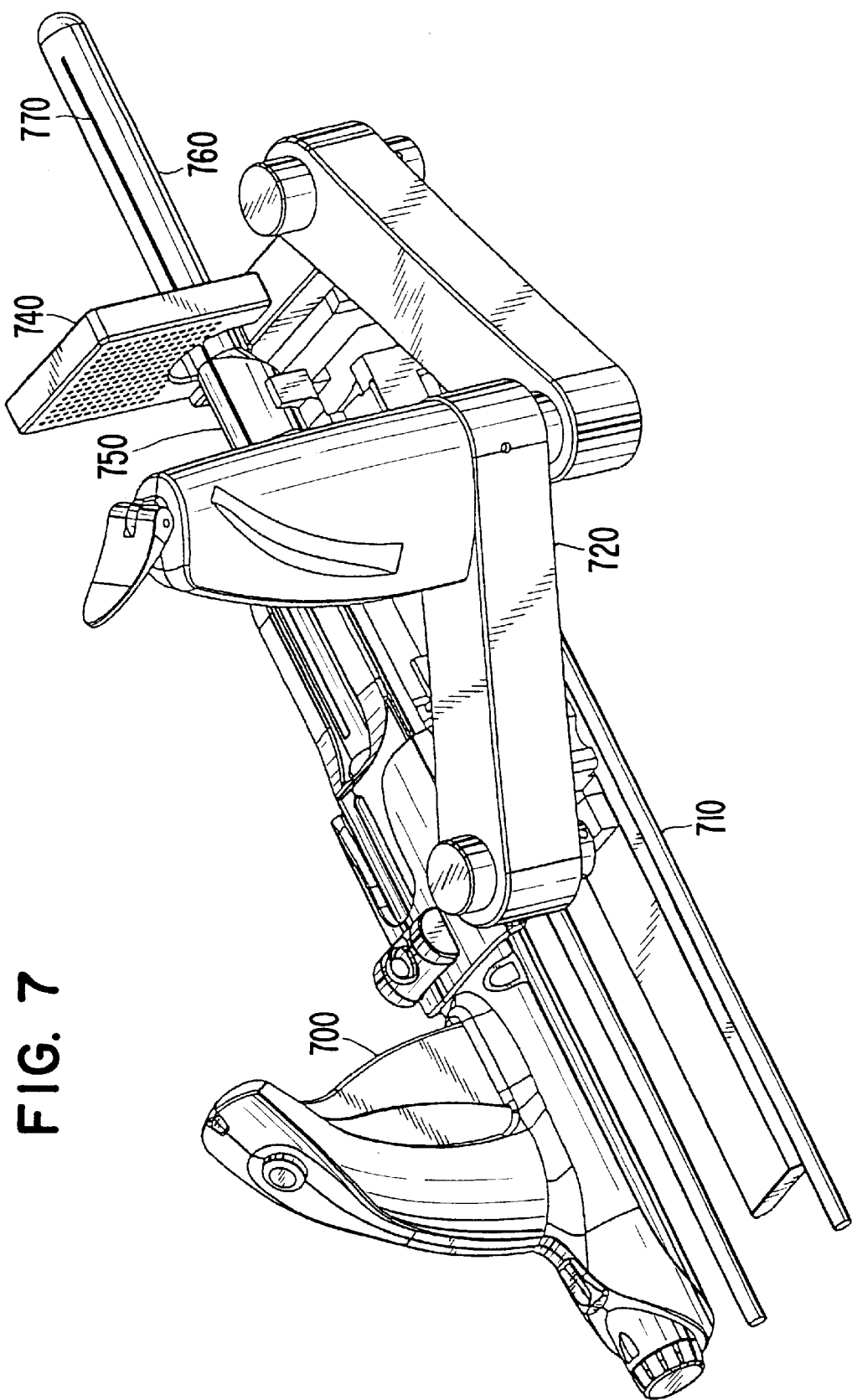
FIG. 7 shows a perspective view of a targeting fixture according to a first embodiment of the invention, coupled to a base unit and with a seed implanting device fitted therein.

The present invention is directed to a targeting fixture for properly positioning a medical instrument with respect to a grid template. FIG. 7 shows a first embodiment of a targeting fixture 720 according to the present invention in a perspective view, with a seed implanting device 700 positioned within the targeting fixture 720, and with the targeting fixture 720 coupled to a mounting unit 710 for a grid template 740. The mounting unit 710 is a conventional device, and typically includes a stepper unit and a base unit. The mounting unit 710 is configured to provide for rotational or inwards/outwards movement with respect to a patient. The mounting unit 710 includes an ultrasound unit 750 and a probe 760, whereby the probe 760 is inserted into a patient's anus, while a needle 770 is inserted into a region that corresponds to the patient's prostate gland. That way, the location of the prostate gland with respect to the grid template 740 can be precisely determined. The grid template 740 is mounted onto a particular location of the mounting unit 710, generally by way of two posts rising from the top of the mounting unit 710.

Details of the medical instrument 700 which is capable of being coupled to the targeting fixture, or more specifically, to a cradle unit or a sheath unit of the targeting fixture, is a subject of a first related application entitled "MEDICAL INSTRUMENT", U.S. Provisional Application No. 60/205,053, filed May 18, 2000, which is incorporated in its entirety herein by reference. Details of a seed cartridge that can be fitted into the medical instrument is a subject of a second related application entitled "CARTRIDGE-MOVEABLE SHIELD", U.S. Provisional Application No. 60/205,055, filed May 18, 2000, which is incorporated in its entirety herein by reference.

Figure 10:
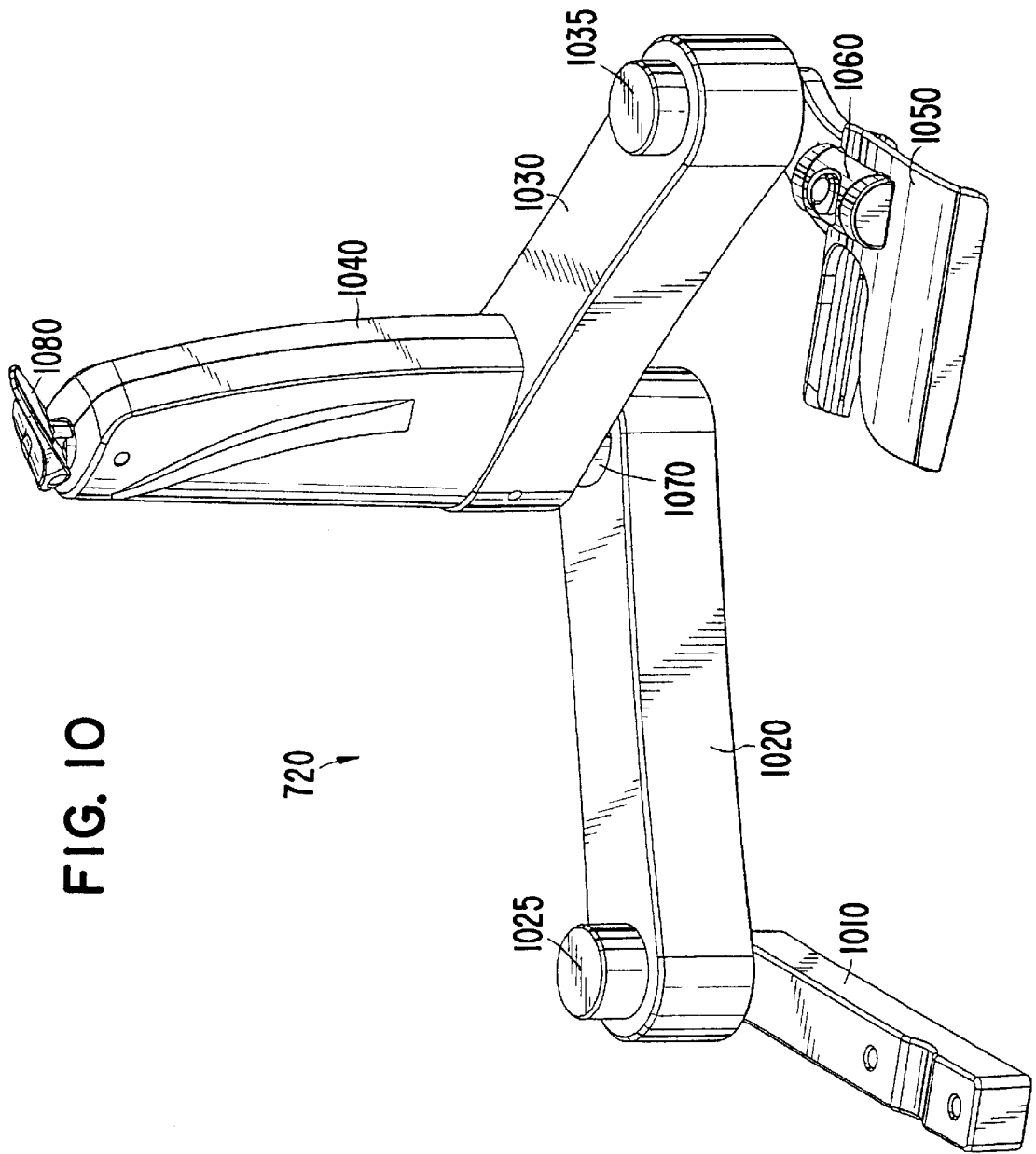
FIG. 10 shows the targeting fixture by itself, according to the first embodiment of the invention.

The targeting fixture 720 is shown by itself in FIG. 10. The targeting fixture 720 includes a boom attachment unit 1010, which has two holes for attaching to the same two posts of the mounting unit 710 that the grid template 740 is also attached to. While FIG. 7 shows the boom attachment unit 1010 disposed on the top posts of the mounting unit 710 below the grid template 740, other ways of attaching the targeting fixture 720 to the mounting unit 710 may be envisioned, while remaining within the scope of the invention.

The boom attachment unit 1010 is pivotably attached to a first arm 1020, by way of a first pivot part 1025. The first arm 1020 is pivotably attached to a second arm 1030, by way of a second pivot part 1070. The second arm 1030 is pivotably attached to a sheath unit 1050, by way of a third pivot part 1035.

Figure 8:
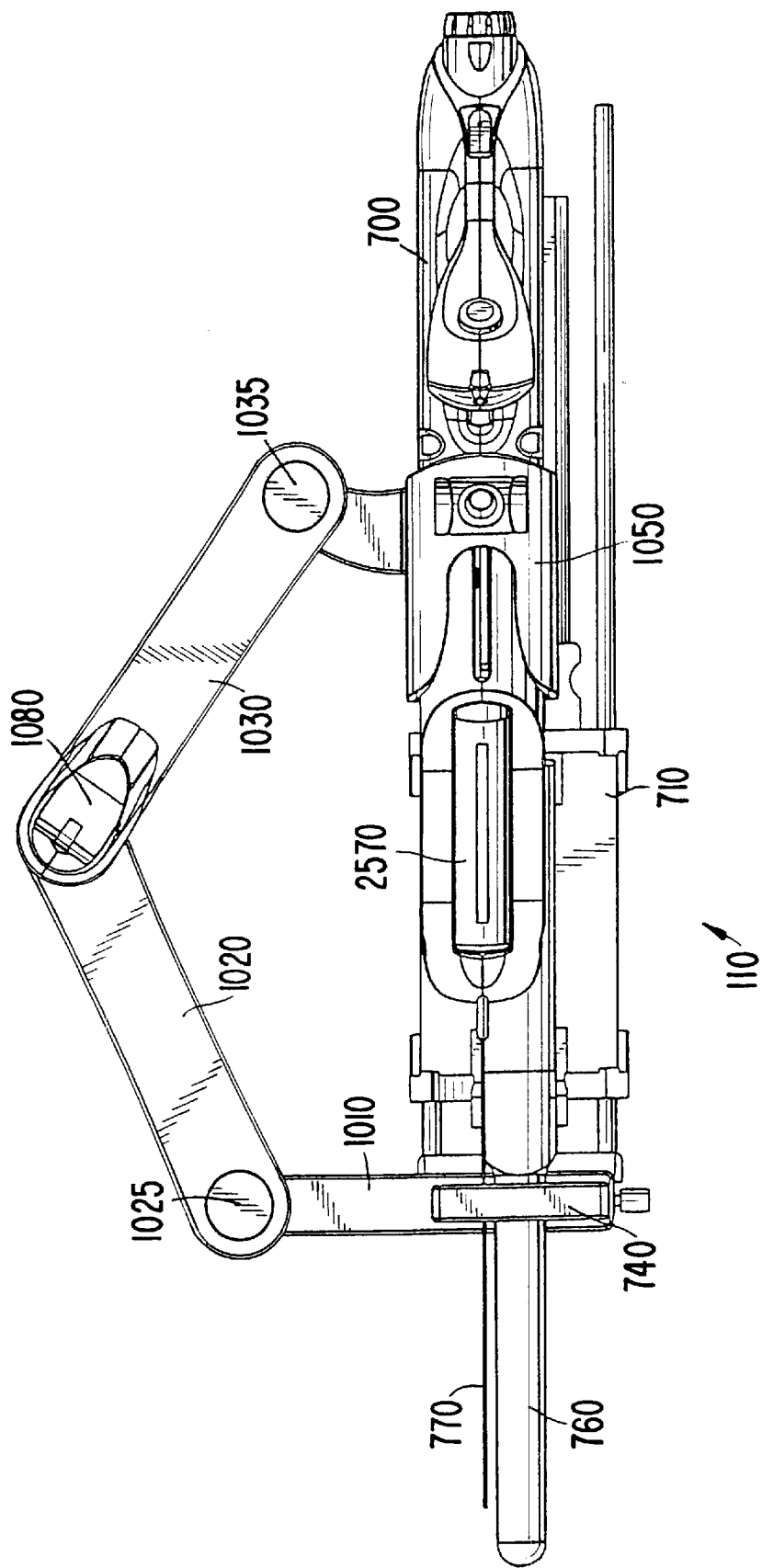
FIG. 8 shows a top view of the targeting fixture according to the first embodiment of the invention, coupled to a base unit and with a seed implanting device fitted therein.

Referring in particular to FIGS. 7, 8 and 10, the first through third pivot parts 1025, 1070, 1035 collectively provide for x-axis and z-axis movement of the sheath unit 1050 (and the medical instrument 700 held in the sheath unit 1050) relative to the grid template 740, while the second pivot part 1070 is coupled to a y-axis movement unit 1040 that allows for the second arm 1030 to be moved in an upwards or downwards direction with respect to the first arm 1020. That is, the combination of the second pivot part 1070 and the y-axis movement unit 1040 provide for y-axis movement of the sheath 1050 relative to the arid template 740. At the topmost part of the y-axis movement unit 1040 is a flapper 1080, which, when released by flipping the flapper 1080 upwards, allows for the targeting fixture 720 to be moved to a desired x,y,z location with respect to the grid template 740, and which, when locked into place by pushing the flapper 1080 all the way down, locks the targeting fixture 720 at the desired x,y,z location.

Each of the elements making up the targeting fixture 720 according to the first embodiment will be described in detail below.

Figure 19:
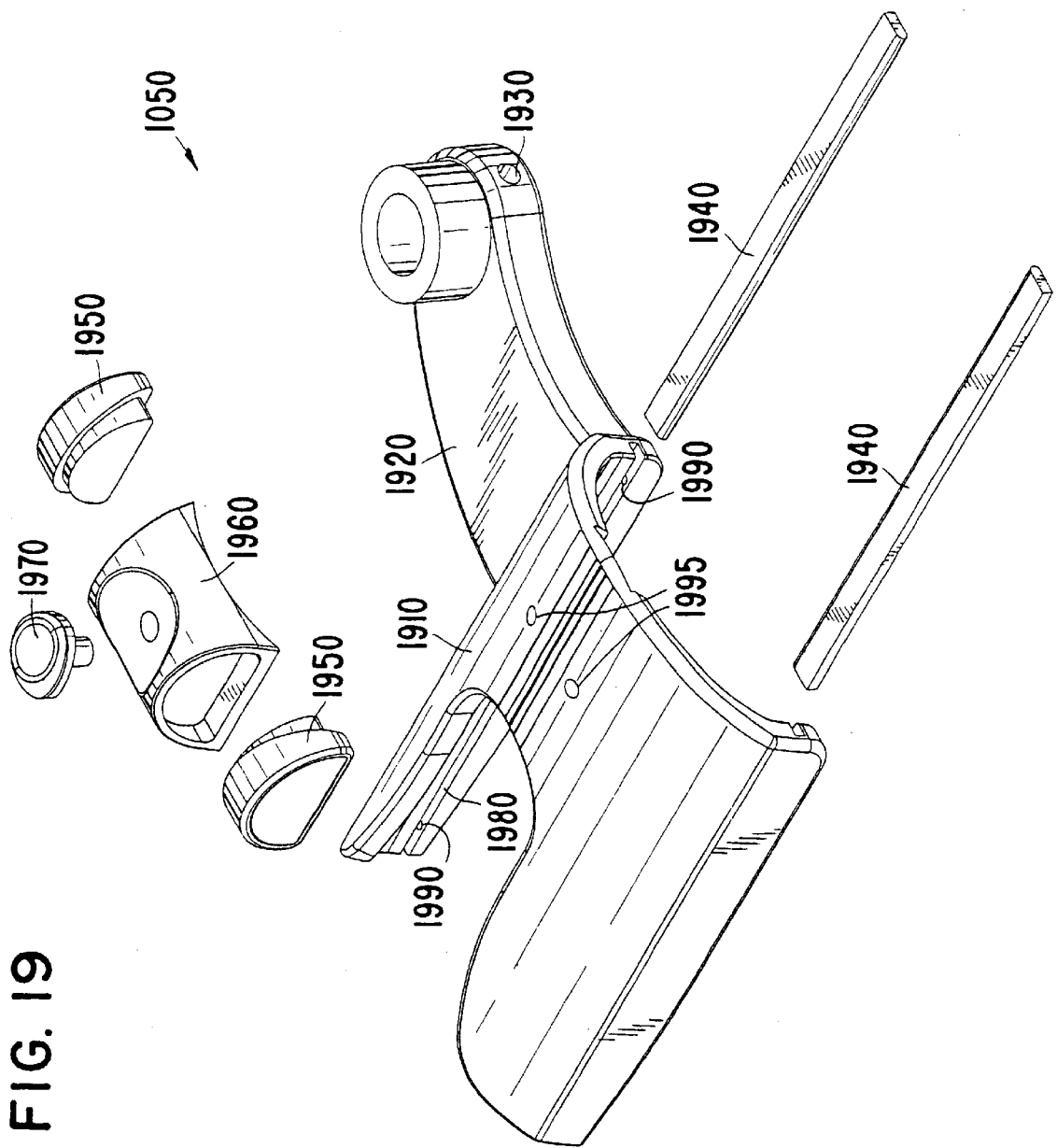
FIG. 19 shows various elements making up a sheath unit, separated from each other for sake of clarity.
Figure 20:
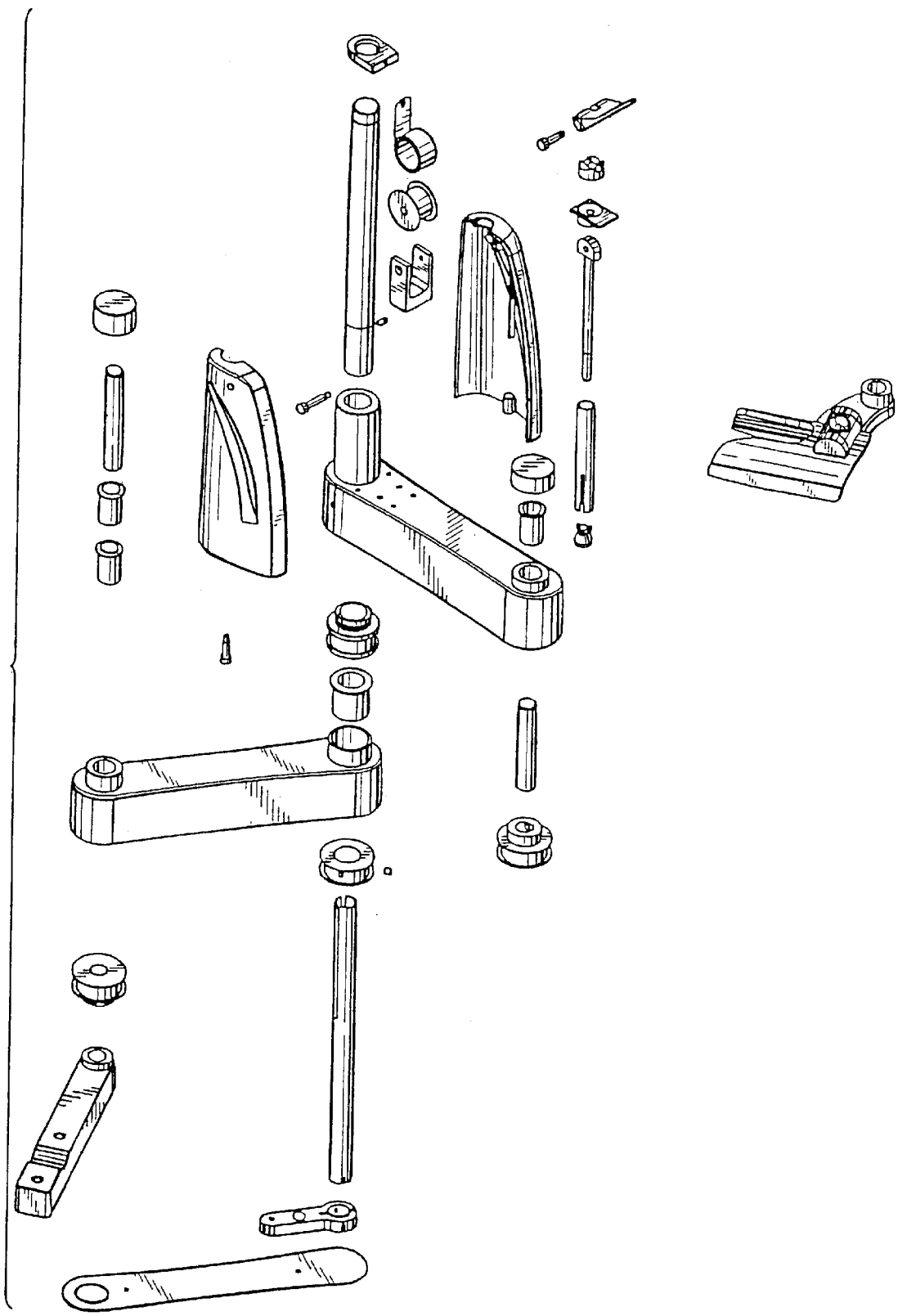
FIG. 20 shows all of the various elements making up the targeting fixture according to the first embodiment.
Figure 22:
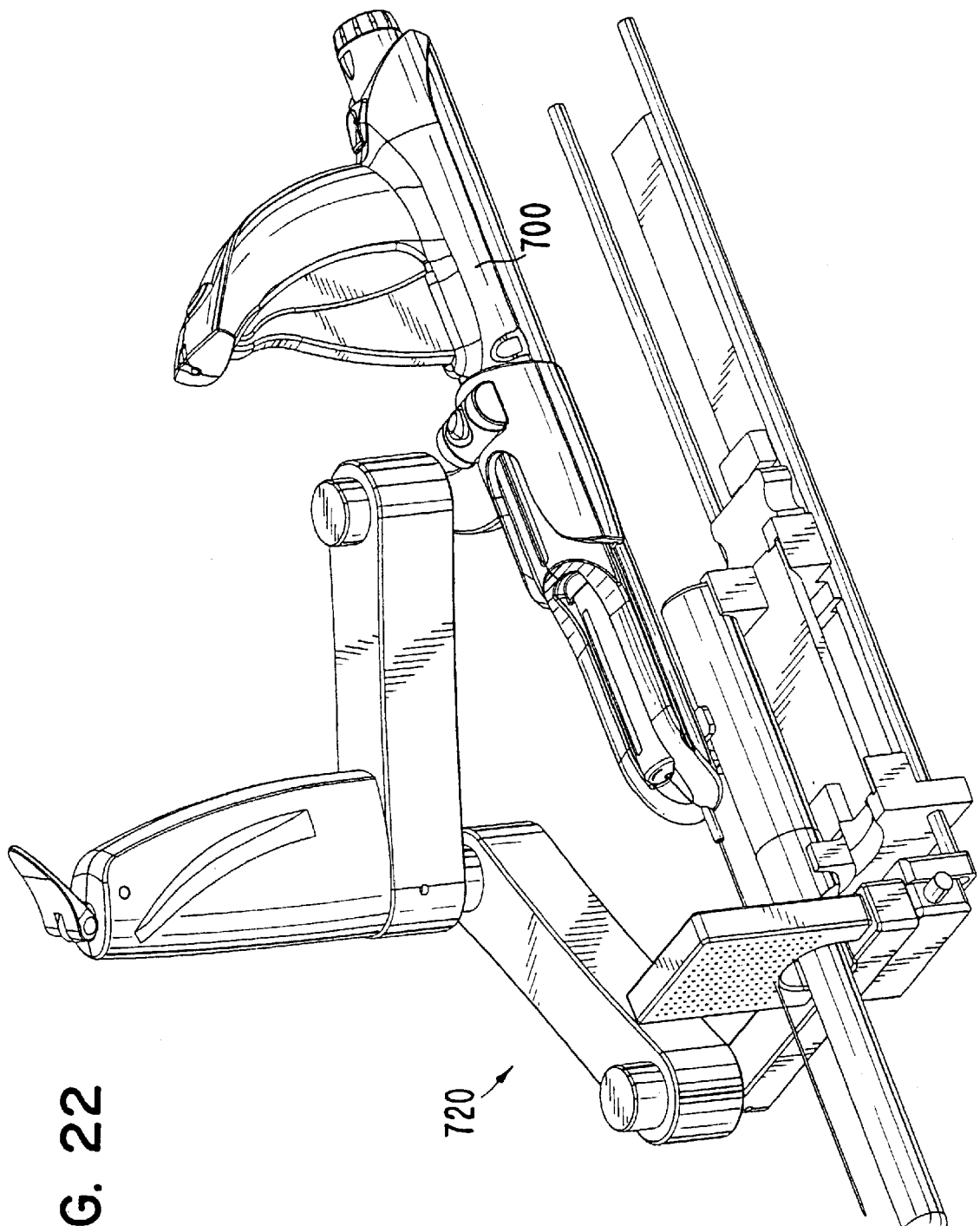
FIG. 22 shows a top perspective view of the targeting fixture according to the first embodiment, attached to a base unit and with a seed implantation device coupled thereto.
Figure 23:
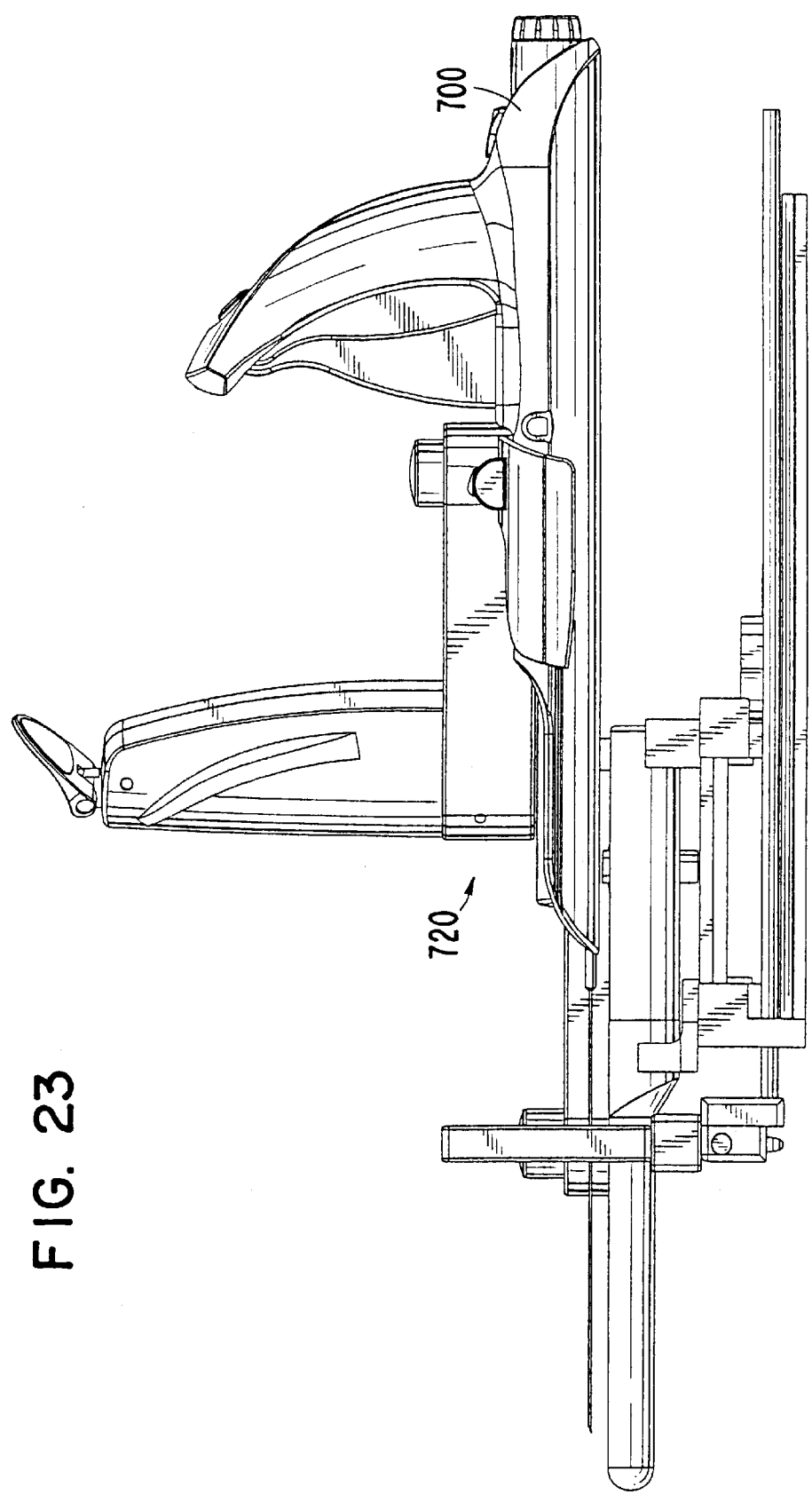
FIG. 23 shows a side view of the targeting fixture according to the first embodiment, attached to a base unit and with a seed implantation device coupled thereto.
Figure 24:
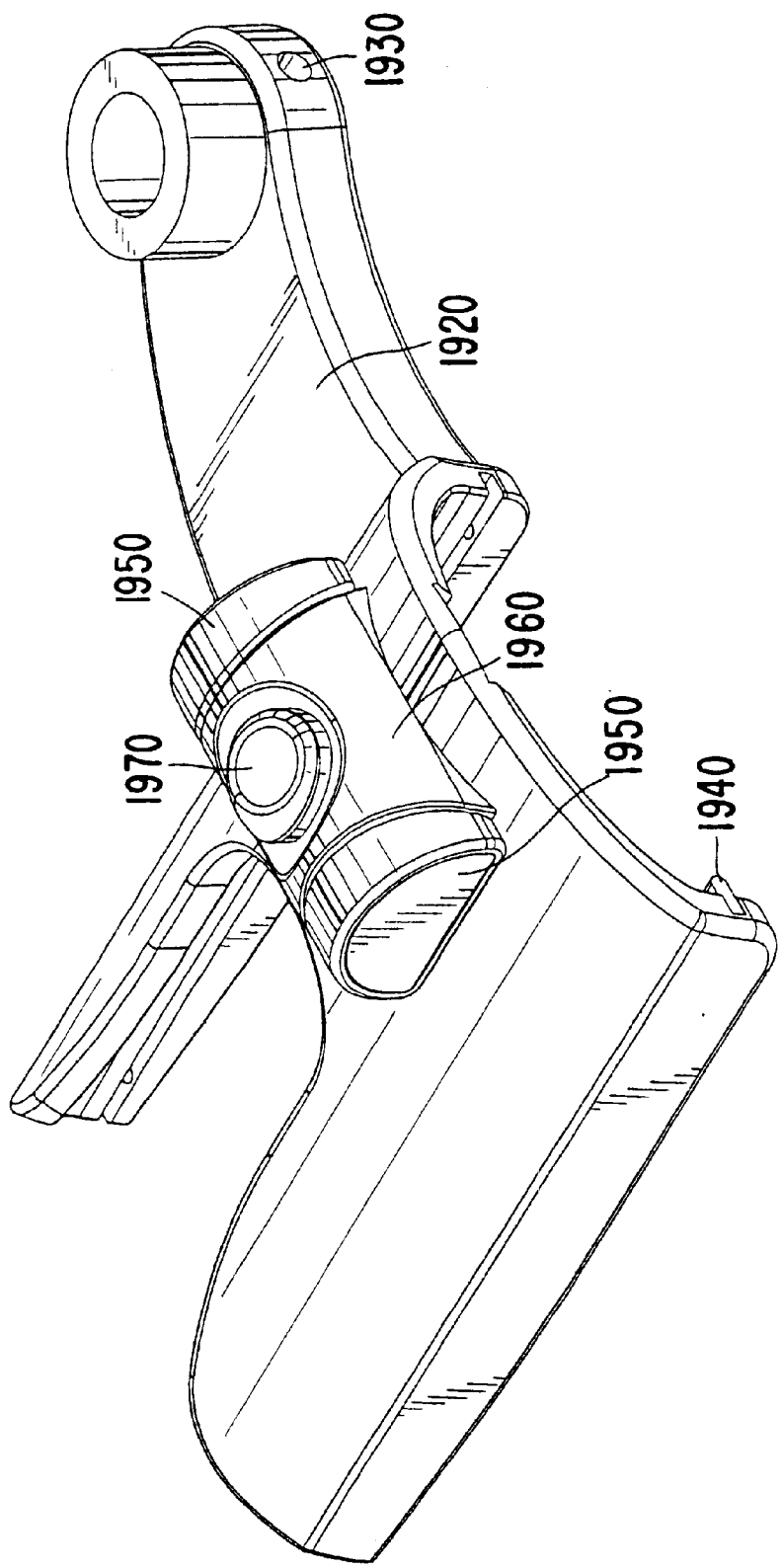
FIG. 24 shows the various elements making up the sheath unit connected together.

FIGS. 19 and 24 shows the sheath unit 1050 in detail. The sheath unit 1050 includes a sheath housing 1910, and a sheath attachment arm 1920 that is integral with the sheath housing 1910 and that attaches to a right side of the second arm 1030 via the third pivot unit 1035. That way, the sheath unit 1050 is capable of axial movement with respect to the second arm 1030. The sheath attachment arm 1920 is attached to the third pivot unit 1035 by way of a set screw that is fitted into the screw hole 1930. The sheath attachment arm 1920 can be removed from the rest of the targeting fixture 720 by unscrewing the screw from the screw hole 1930, to thereby sterilize the sheath unit 1050, for another treatment.

The sheath unit 1050 also includes slots 1980 (only one can be seen in FIG. 19, but see FIG. 9) on opposite sides of the sheath housing 1910. A key way 1940 is respectively provided in each of the slots 1980. Each key way 1940 is preferably a lubricated plastic part, and juts out of its respective slot 1980 in order to engage with a side of a medical instrument (see FIG. 9, left side of sheath unit, and also see FIG. 25 that shows the housing of a medical instrument 700) that has a corresponding groove that accepts the slot 1980. The key ways 1940 are held in place within the slots by way of set screws (not shown), which are screwed in via screw holes 1990. The sheath unit 1050 is preferably an aluminum unit, except for the key ways 1940. The key ways 1940, as well as the other parts of the sheath unit 1050, are preferably autoclaveable, so as to be sterilized for reuse.

Figure 25:
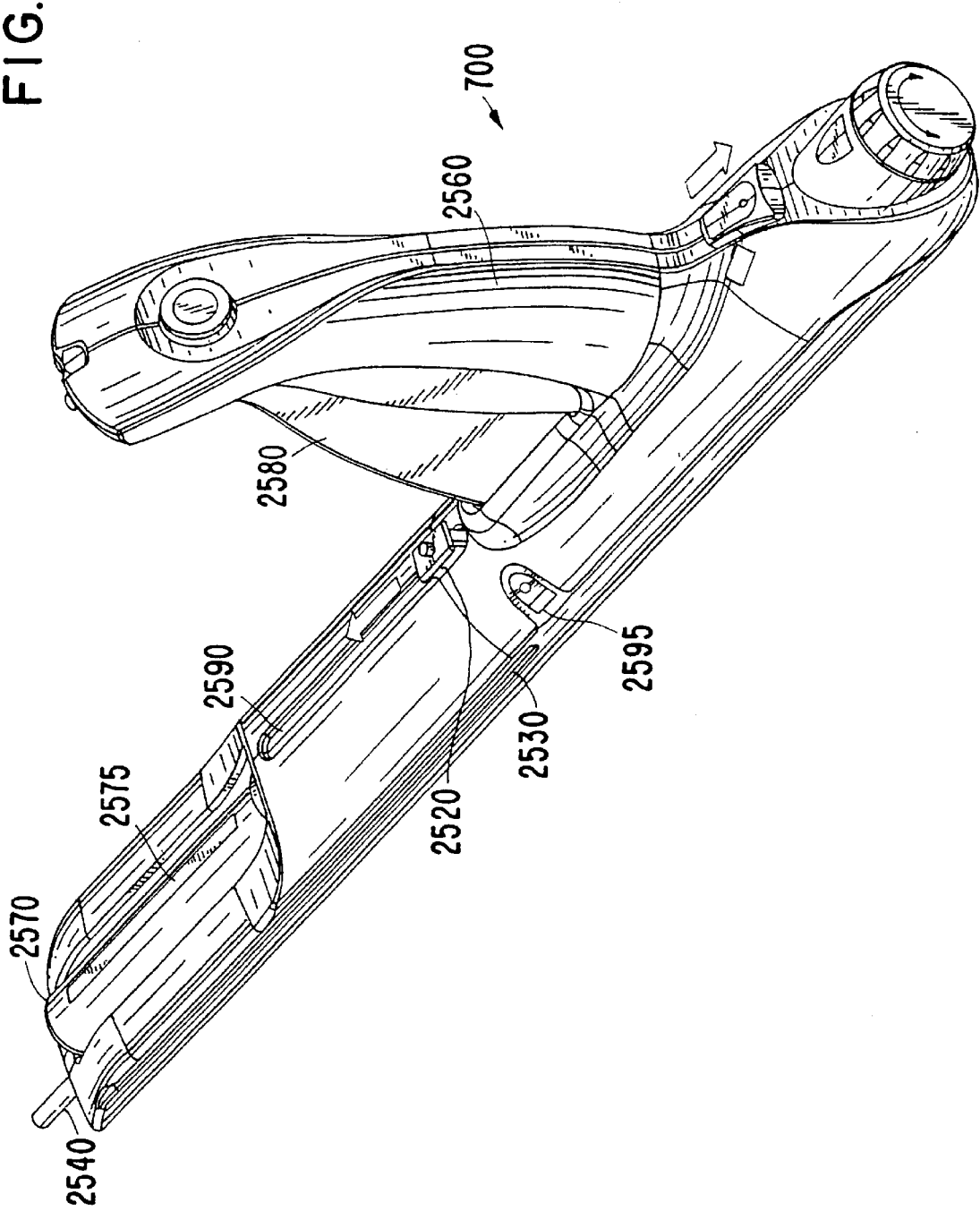
FIG. 25 shows a seed implantation device that is configured to couple to the sheath unit of FIG. 24.
Figure 26:
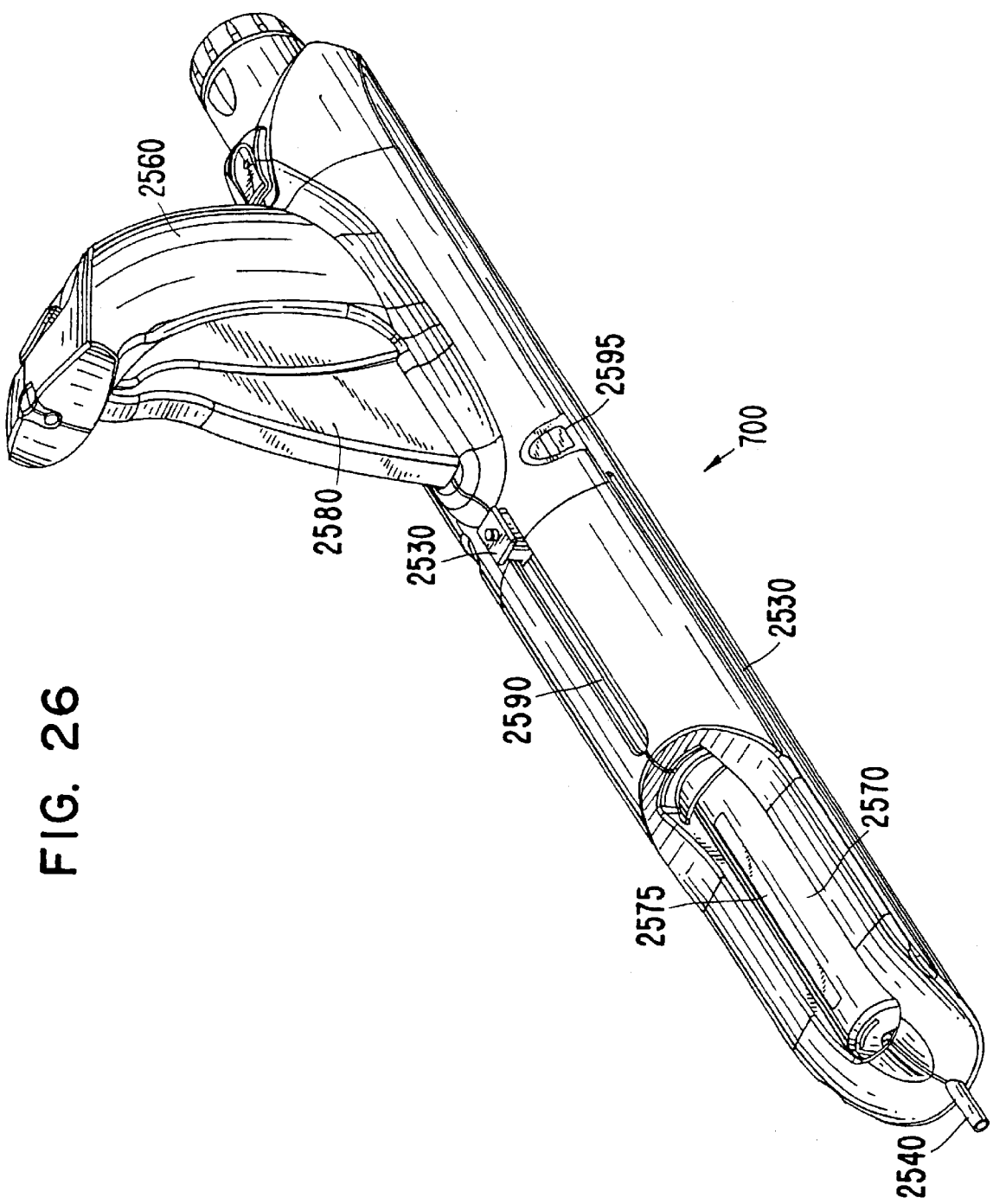
FIG. 26 shows a different view of the seed implantation device of FIG. 25.

The sheath housing has a U-shaped opening at its top portion. The length of this U-shaped opening is preferably the size of a large prostate gland, typically about 3 inches in depth. Also shown in FIG. 19 are two holes 1995, on which a cylindrical element 1960 is fitted therein by way of screws (not shown). The cylindrical element 1960 is fitted with first and second side buttons 1950, and a top button 1970. The functions of these buttons will be explained later. In short, the first and second side buttons 1950 are simultaneously engaged by pushing both of them inwards, and this action allows a feature of the medical instrument 700 to move. That feature corresponds to a nut box interface 2520 as shown in FIGS. 25 and 26, and it couples to an element (not shown) on the bottom of the upper surface of the sheath housing 1910.

When the targeting fixture 720 is placed into its proper position with respect to the grid template 740, the medical instrument 700 can be inserted and held in place within the sheath unit 1050. Side slots 2530 of the medical instrument 700 are fitted onto the key ways 1940 of the sheath unit 1050, and the medical instrument 700 is pushed in a direction towards the grid template 740. The medical instrument 700 is locked in place when the nut box interface 2520 couples to the element on the bottom of the upper surface of the sheath housing 1910. In the preferred embodiment, a clicking sound is heard at that time, informing the user that the medical instrument 700 is correctly positioned within the sheath unit 1050. When the medical instrument 700 is clicked into place, it also engages with the needle 770, by way of the needle nozzle (see element 2540 of FIGS. 25 and 26) of the medical instrument 700.

When the top button 1970 of FIG. 19 is pushed downwards from its normal, upwards position, the nut box interface 2520 of the medical instrument 700 disengages from the sheath unit 1050, allowing the medical instrument 700 to be removed by sliding it back out of the sheath unit 1050.

Referring now to FIGS. 7 and 8, the medical instrument 700 includes a handle 2560 (see FIGS. 25 and 26), which has an actuator by which a user can push inwards to eject a seed out of the medical instrument and into a needle, and thereby into a patient. The medical instrument 700 is shown as having a cartridge accepting region for accepting a cartridge 2570 (see also FIGS. 25 and 26) that contains seeds. The cartridge accepting region is located at a portion of the medical instrument 700 adjacent to the needle nozzle 2540. The cartridge 2570, which includes a seed capacity indicator 2575, is the subject of another co-pending application.

As a seed is fired from the medical instrument 700 and into a patient by way of the needle 770, the medical instrument 700 backs out from the sheath unit 1050 in a direction away from the grid template 740. In more detail, as a trigger mechanism 2580 on the handle 2560 of the medical instrument 700 is engaged by a predetermined amount, a seed is removed from the cartridge 2570 by the medical instrument 700, and the seed is pushed into the needle 770. As the user continues to engage the trigger mechanism 2580 past the predetermined amount, the medical instrument 700 moves back away from the grid template 740.

As the medical instrument 700 moves backwards in a direction away from the grid template 740, while still mounted in the sheath unit 1050, the nut box interface 2520 moves from its initial location at its most proximal position, to a position that approaches the proximal end of the medical instrument 700. In other words, as the trigger mechanism was pressed to move the medical instrument 700 back away from the grid template 740, the nut box interface 2520, which is grabbed by an element on the bottom surface of the top part of the sheath housing 1910, is held in position while the rest of the medical instrument 700 moves backwards with respect to it.

The nut box interface 2520 is capable of movement longitudinally within the slot 2590 in which it is disposed on the top side of the medical instrument 700, as seen in FIGS. 25 and 26. The slot distance is approximately the depth of a largest prostate gland. The stroke of the medical instrument 700 is determined by this slot distance. Once the medical instrument 700 has moved the entire distance of the slot 2590, the nut box interface 2520 cannot move any further, and the medical instrument 700 has to be reset back into its "zero" position within the sheath unit 1050. The resetting is by way of a user pushing against the first and second side buttons 1950 in FIG. 19, which releases the nut box interface 2520 from a drive screw (not shown) of the medical instrument 700 to which it is normally attached, thereby allowing a user to push the medical instrument 700 within the sheath unit 1050 back to its most-proximal position with respect to the grid template 740. When the first and second side buttons 1950 are released, the nut box interface 2520 re-engages with the drive screw.

At the proximal end of the medical instrument 700 of FIG. 7 is a pitch adjustment knob, which can be set to a position to move the medical instrument 700 backwards by a desired amount due to a single seed implant. The pitch adjustment knob may be moved from position to position between seed firings, based on a particular pre-plan being accomplished during a treatment of a patient.

Also shown in FIGS. 25 and 26 is a vernier feature 2595 provided on each side of the medical instrument 700. The vernier feature 2595 informs a user as to the exact z-position during a seed-implanting process. In more detail, the vernier feature 2595 corresponds to a 0 to 3" scale provided on both sides of the medical instrument 700, whereby a window slides over a particular numeric indicator on that scale to inform the user as to the depth of the needle with respect to the proximal and distal ends of the prostate gland. In other words, the vernier feature 2595 informs that user as to how far in the z-direction the medical instrument 700 has moved.

Figure 9:
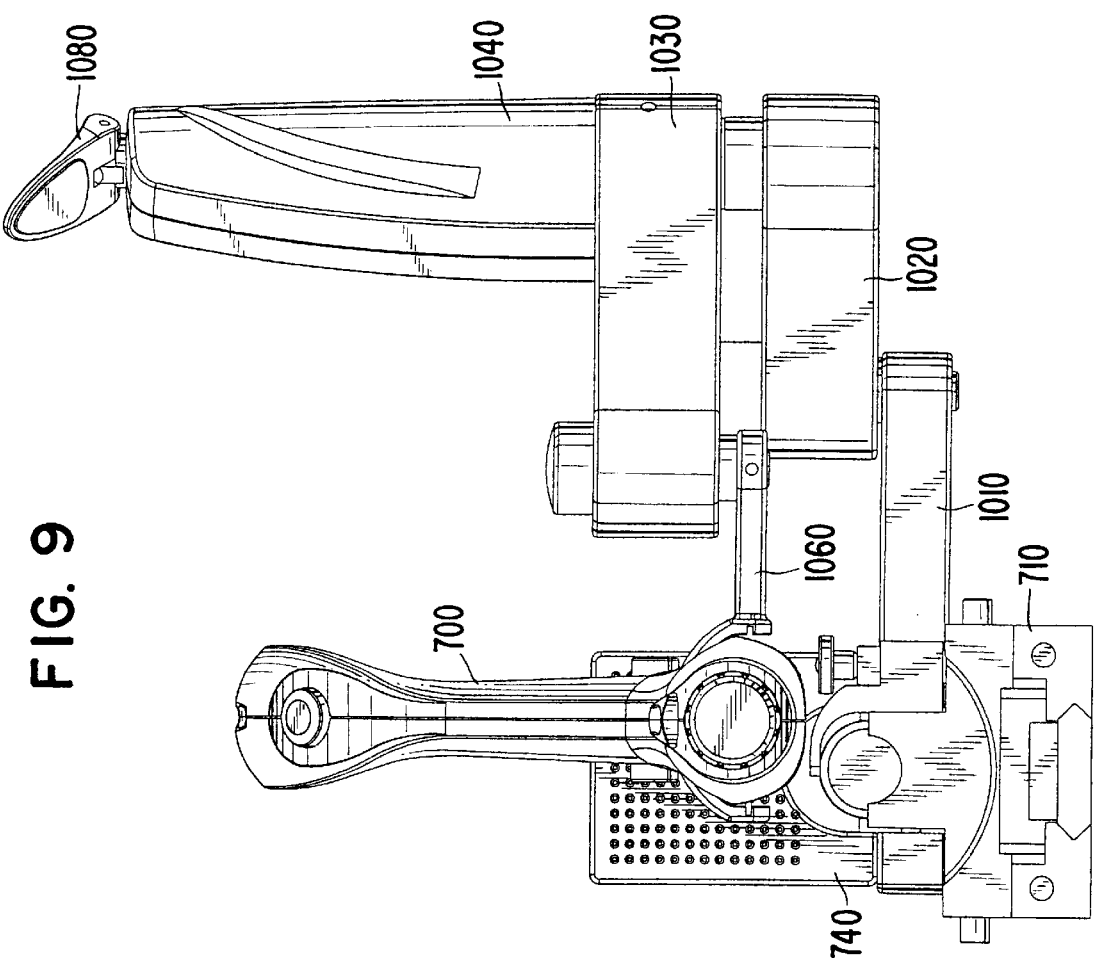
FIG. 9 shows a back view of the targeting fixture according to the first embodiment of the invention, coupled to a base unit and with a seed implanting device fitted therein.

Other elements comprising the targeting fixture 720 of the first embodiment will now be explained in detail. FIG. 9 shows the flapper 1080 in the upward position, thereby allowing a user to manipulate the targeting fixture 720 to place it in a desired x,y,z position with respect to the grid template 740. The x,y position allows the targeting fixture 720 to be positioned accurately with respect to a particular grid location, such as "C-5", of the grid template 740, and the z-position allows the targeting fixture 720 to be positioned accurately with respect to the zero plane (most distal point of the prostate gland), so as to be in a precise position in order to begin applying seeds to a patient's prostate gland. Once the targeting fixture 720 is placed in the correct x,y,z position, the flapper 1080 is flipped down, to thereby lock the targeting fixture 720 in place. The doctor can accurately set the x,y position visually with respect to a particular grid position on the grid template 740, and the z-position can be set by way of the doctor knowing the correct depth amount from the ultrasound unit of the base unit 710, when the needle is placed into the patient's prostate gland.

Thus, with the first embodiment, engaging one feature, that being the flapper 1080, allows for release of all x, y and z-motion of the targeting fixture 720 simultaneously, to allow repositioning of the boom assembly making up the targeting fixture 720.

The first and second arms 1020, 1030 of FIG. 10 can rotate relative to each other, thereby allowing for the targeting fixture 720 to be positioned to a desired x,z location with respect to the grid template 740. The y-axis movement unit 1040 is shown in FIG. 10 as a housing, where the components that allow for y-axis movement of the targeting fixture, and where most of those components are provided within the housing 1040, are shown in FIGS. 11–18.

Figure 11:
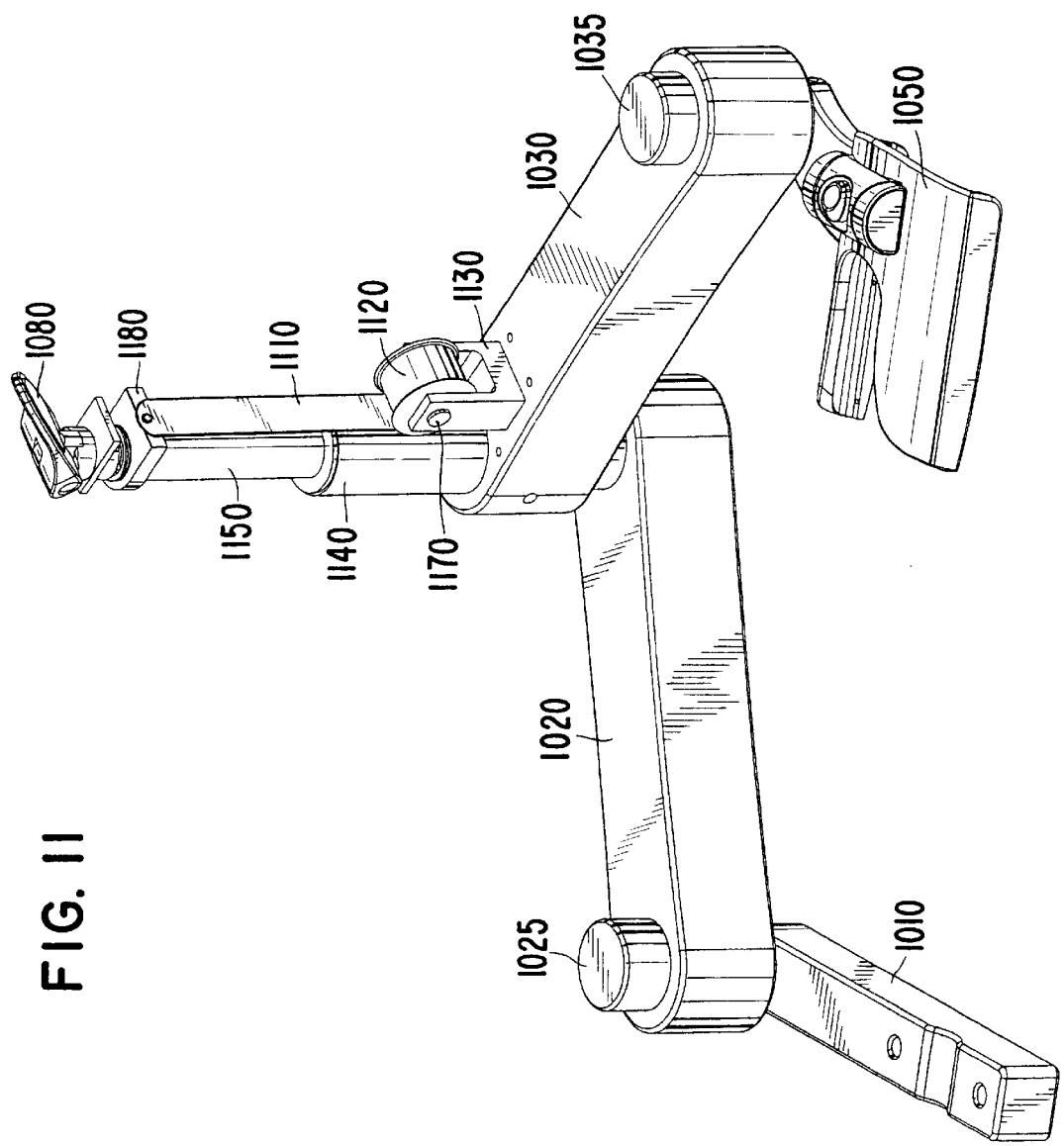
FIG. 11 is similar to FIG. 10, but with a housing for the y-axis movement assembly removed.

FIG. 11 shows a constant force spring unit that includes a tape 1110 that is attached at one end to a nut 1180, and that is attached at its other end and wound around a drum 1120. The constant force spring unit also includes a drum 1120 that rotates with respect to a pivot point 1170, where the drum is situated with a U-shaped bracket 1130 that also forms part of the constant force spring unit. The U-shaped bracket 1130 is attached to a top surface of the second arm 1030.

The constant force spring unit is constructed so as to allow the second arm 1030 to be able to move up and down with respect to the vertical shaft 1150, and thereby move up and down with respect to the first arm 1020. The second arm 1030 is always positioned above the first arm 1020, however. The constant force spring unit is constructed so as to balance the weight of the medical instrument, the sheath unit 1050 and the second arm 1030. That is, to the user, there does not seem to be any force required to manipulate the instrument in an upwards or downwards direction, due to the constant force spring unit being provided in the targeting fixture 720. In the preferred embodiment, the targeting fixture 720 is moved in the y-direction by a user pulling the medical instrument 700 up or down by way of the handle of the medical instrument, and not be the user actually touching the second arm 1030 itself. As the medical instrument 700 is moved upwards, with respect to the position of the targeting fixture 720 shown in FIG. 11, the second arm 1030 and the drum 1120 attached to the second arm 1030 move upwards due to their being connected to the sheath unit 1050 on which the medical instrument 700 is also slotted into. This action results in the tape 1110 winding into the drum 1120 as the drum 1120 (actually the second arm 1030 on which the drum 1120 is disposed) moves upwards, and the constant force spring unit holds the structure in place wherever the positioning is left at. The constant force spring unit provides the same amount of force at any y-position of the second arm 1030 with respect to the first arm 1020, due to it being balanced to the medical instrument 700. That way, the second arm 1030 is held in place no matter where it is situated with respect to the vertical shaft 1150.

Also shown in FIG. 11 is a mid-diameter element 1140, which contains bearings that allows it to ride up and down the vertical shaft 1150. This allows the structure that includes the second arm 1030, the sheath unit 1050 and the medical instrument 700 to move up and down the vertical shaft 1150.

While the above description has been made with respect to a mechanism that provides vertical movement of one boom arm with respect to another boom arm, other ways of performs such movement may be envisioned while remaining within the scope of the invention.

Now, a structure that maintains a precise angular relationship between the first and second arms 1020, 1030, will be described in detail below. Such a structure is used so that the sheath unit 1050, and thus the medical instrument 700 fitted into the sheath unit 1050, are always orthogonally-lined up with a front face of the grid template 740. Thereby, there does not exist a problem due to misalignment of the medical instrument 700 to the needle 770.

Figure 12:
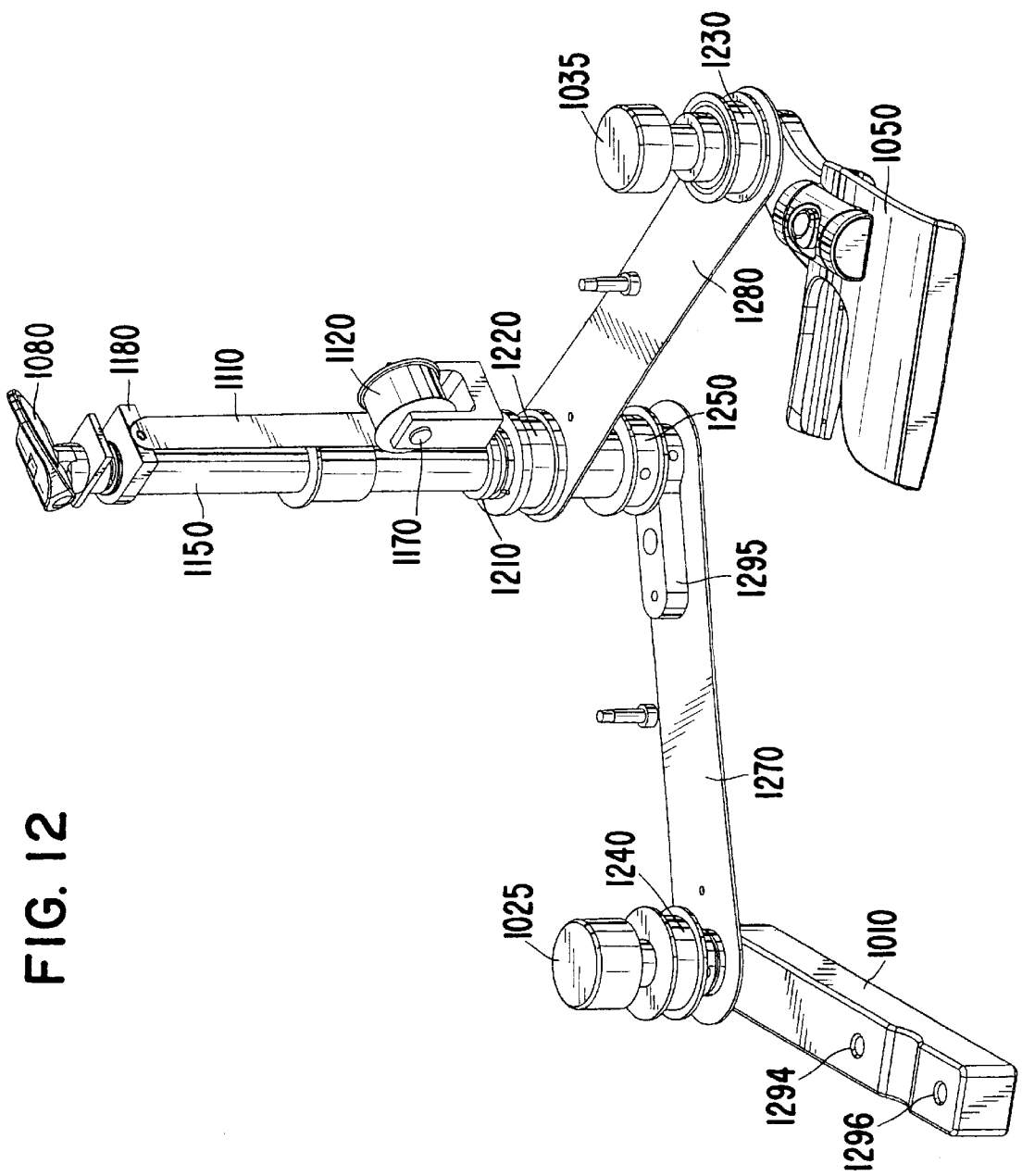
FIG. 12 is similar to FIG. 11, but with covers for the arms removed.
Figure 13:
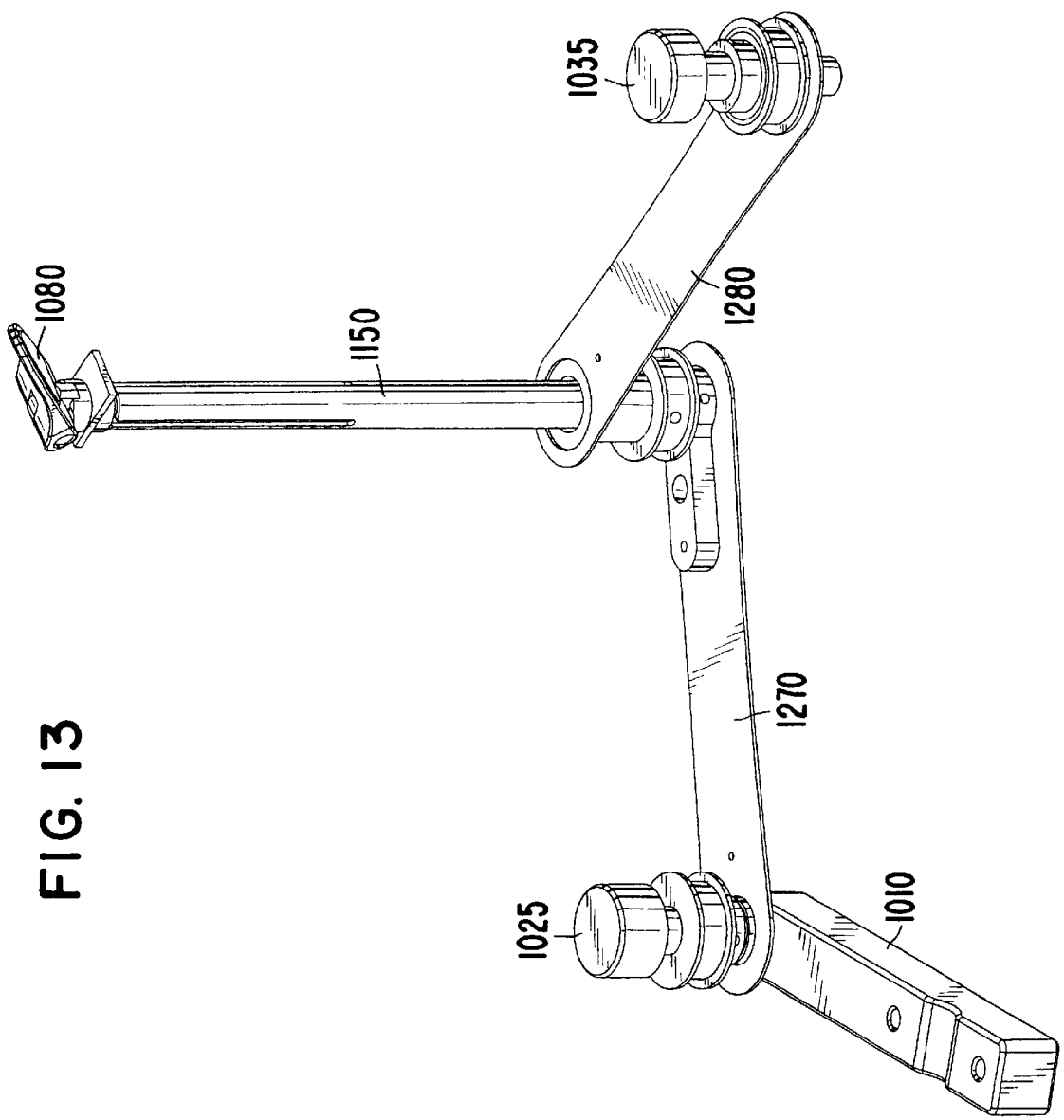
FIG. 13 is similar to FIG. 12, but with elements on the vertical shaft removed.
Figure 14:
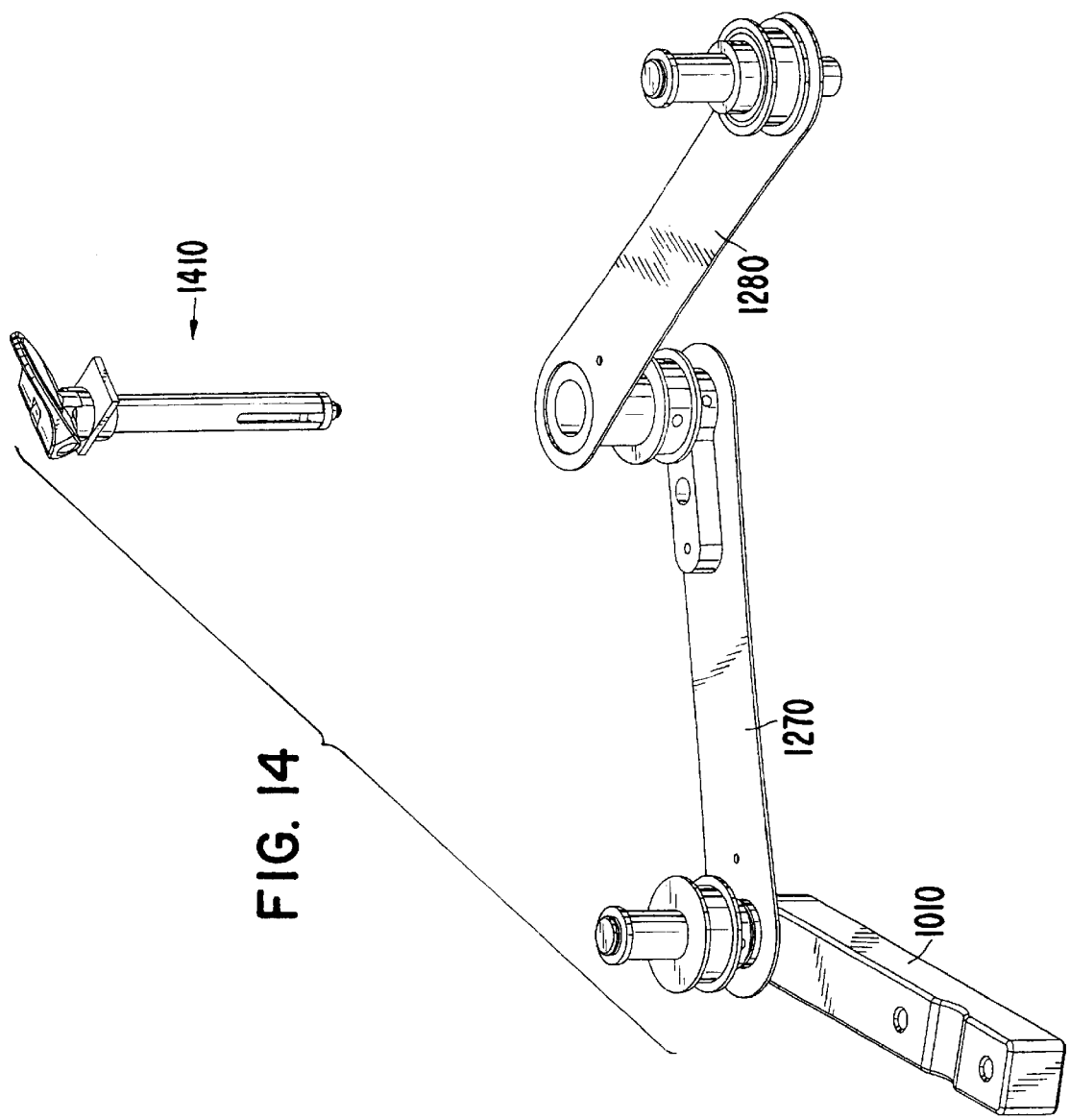
FIG. 14 shows the disposition of various elements used in the y-axis movement assembly.

FIG. 12 shows the pivot connections between the various elements of the targeting fixture 720, with the outer housings of the first and second arms 1020, 1030 removed (see FIG. 11 where those housings are shown), in order to show the elements within the first and second arms 1020, 1030. Within the first arm 1020 is a first pulley 1240 and a second pulley 1250. The first pulley is coupled to the first pivot unit 1025, and the second pulley 1250 is coupled to the second pivot point 1070. The second pulley 1250 is shown as being disposed on top of an arm shaft lock link 1295. Note that the boom attachment unit 1010, which is also coupled to the first pivot point 1025, is shown having two holes 1294, 1296, which are for attaching to the same two posts of the mounting unit 710 that the grid template 740 is also attached to. These two holes 1294, 1295 define the plane corresponding to a front face of the grid template 740 (see FIG. 7, for example). In the present invention, the sheath unit 1050, and thus the medical instrument 700 fitted therein, is always maintained parallel to the axis of a needle inserted into the grid template 740, or in other words the sheath unit 1050 is always maintained so that its longitudinal axis is orthogonal to the plane corresponding to the front face of the grid template 740.

In FIG. 12, only the bottom cover panels 1270, 1280 for the first and second arms, respectively, are shown for sake of clarity. The first and second pulleys 1240, 1250 are respectively provided within the first arm 1020, and which rotate with the first and second pivot units 1025, 1070. FIG. 12 also shows third and fourth pulleys 1220, 1230, which are respectively provided within the second arm 1030, and which rotate with the second and third pivot units 1070, 1035. Not shown in FIG. 12 is a first timing belt that is fitted around the first and second pulleys 1240, 1250, and a second timing belt that is fitted around the third and fourth pulleys 1220, 1230. The first and second timing belts are provided with teeth that engage corresponding teeth (not shown) of the first through fourth pulleys. Also shown in FIG. 12 is a keyed pulley assembly 1210, which keys the third pulley 1220 with respect to the vertical shaft on which it is disposed. That way, the third pulley 1220 on the second arm bottom cover panel 1280 is keyed to the second pulley 1250 on the right side of the first arm bottom cover panel 1270 (with the arm shaft lock link 1295 disposed between the second pulley 1250 and the first arm bottom cover panel 1270).

With this configuration, the first and second arms 1020, 1030 rotate in concert with each other, in such a way that the first and second arms 1020, 1030 can only rotate with respect to each other so as to maintain the orthogonal relationship between the longitudinal axis of the sheath unit 1050 and the plane corresponding to the front face of the grid template 740.

Figure 15:
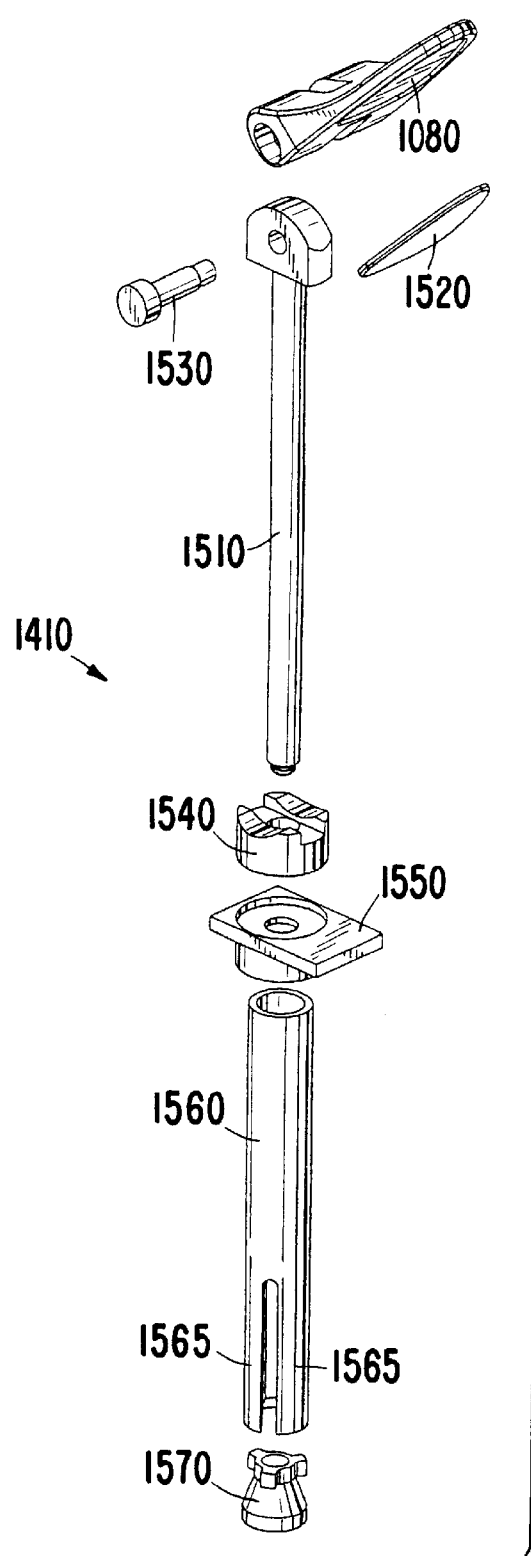
FIG. 15 shows various elements making up a tensioning device for the y-axis movement assembly, separated from each other for sake of clarity.

As explained above, the constant force spring unit provides the necessary amount of force to hold the targeting fixture 720 in a particular y-position. The first embodiment also includes a mechanism for adjusting the tension of the y-axis movement structure. FIG. 15 shows the various elements making up a cam lock assembly 1410. The flapper 1080 is fitted onto a center shaft 1510, by way of a shoulder screw 1530. The flapper 1080 also includes a lower flap element 1520. The center shaft 1510 is fitted onto a slotted nut 1540, and it goes through a cam lock assembly piece 1550. The cam lock assembly piece 1550 holds the top end of the tape 1110 of the constant force spring unit (see FIG. 12, for example). The center shaft 1510 is fitted within a tube 1560, which has three fingers 1565 at its bottom end provided by way of three slots at the bottom portion of the tube 1560 (only one slot can be seen in FIG. 15). The tube 1560 engages a bottom cone piece 1570. The bottom cone piece 1570 is fitted within the three slots of the tube 1560, so that it cannot rotate.

Figure 16:
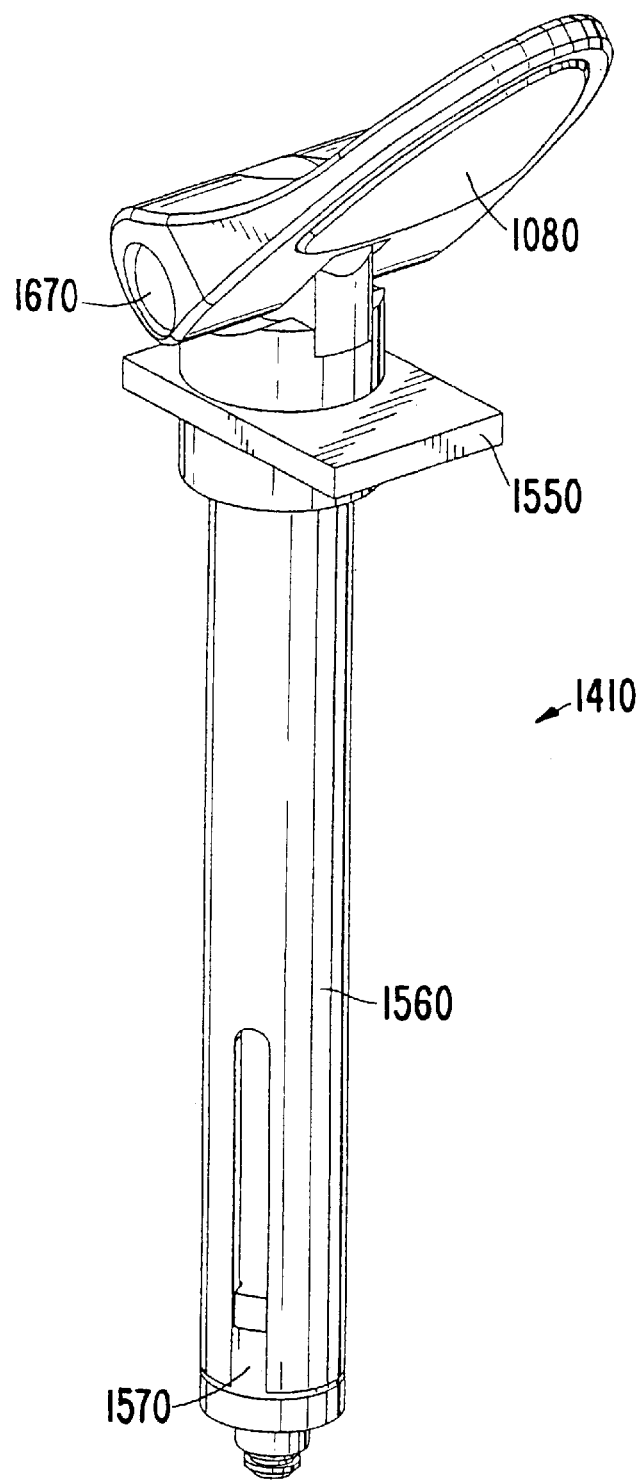
FIG. 16 shows the elements of FIG. 15 coupled together to form a tensioning assembly.

At the top, the flapper 1080, and thus the center shaft 1510, can be rotated either clockwise or counterclockwise, in order for the user to obtain a fine adjustment on the cone piece 1570, for the y-axis movement. Referring now to FIGS. 15 and 16, the flapper 1080 has an eccentric hole 1670. When the flapper 1080 is rotated, the outside boundary around the eccentric hole 1670 of the flapper 1080 acts as a cam, and it rubs against the slotted nut 1540, which is preferably a smooth part that allows the flapper 1080 to rotate without much friction between those parts. As a consequence, the center shaft 1510 moves vertically up and down.

To adjust the tension of the y-axis movement assembly, the flapper 1080 is rotated clockwise. This rotation causes the cone 1570 to screw upwards on the teeth provided at the bottom of the center shaft 1510, and this action puts more tension on the fingers 1565 of the tube 1560 due to the cone 1570 moving upwards. Once a sufficient initial tension has been found, as determined by the user, the flapper 1080 can then be rotated to generate a cam surface which forces the center shaft 1510 to move upwards. This generates a large amount of force through the nut of the cone piece 1570, which splays the tube fingers 1565 outwards against the tube 1560 that it is inserted into.

Figure 17:
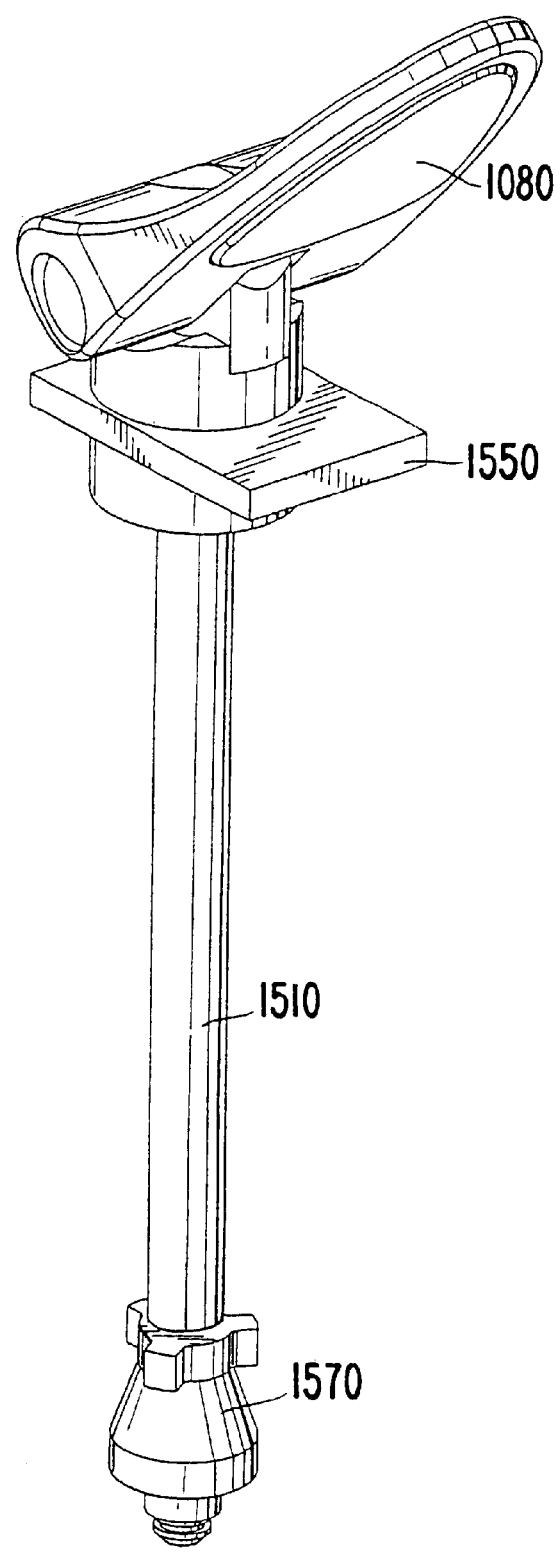
FIG. 17 is similar to FIG. 16, but with a tube removed for sake of clarity.

FIG. 17 shows the cone piece 1570 coupled to the bottom of the center shaft 1510, where the tube 1560 is not shown for sake of clarity.

Figure 18:
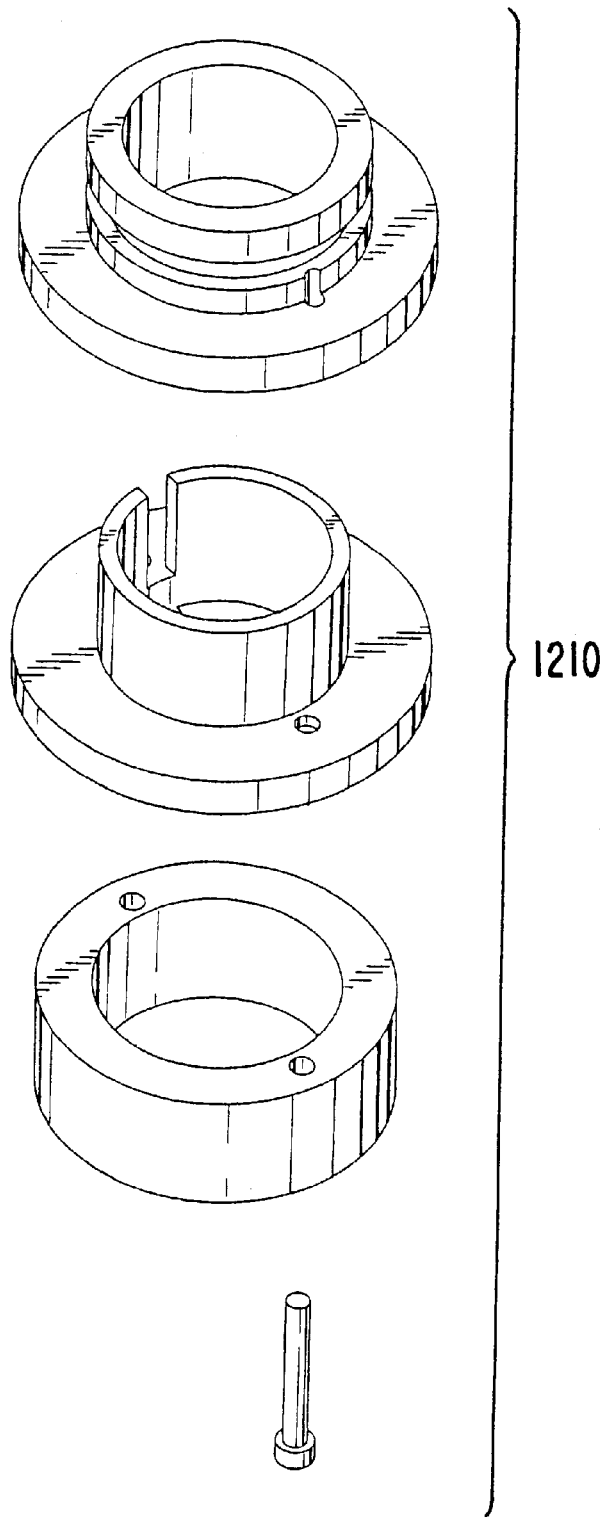
FIG. 18 shows elements making up a keyed pulley assembly.

FIG. 18 shows the various elements making up the keyed pulley assembly 1210, which is essentially a bushing feature which holds the center shaft 1510 in place. The keyed pulley assembly is disposed within the mid-diameter element 1140 (see FIG. 11).

A second embodiment of a targeting fixture according to the invention will now be described. FIG. 1 shows a targeting fixture 110 according to the second embodiment, which is coupled to a base unit and in which a medical instrument is fitted therein.

The targeting fixture 110 includes a first hinge 130 that is coupled to an element 130 that can be rotated with respect to a structure 105 that surrounds the grid template 740. The first hinge 130 is pivotably connects the rotatable element 130 to a first arm 140, where the first arm provides for up/down movement. The first arm 140 is pivotably connected to a second arm 150 by way of a second hinge 145. The other end of the second arm 150 is pivotably connected to a sheath unit 160 by way of a third hinge 155. A medical instrument 160 is fitted into the sheath unit 160, in a manner similar to that described with respect to the first embodiment. This structure allows the medical instrument to be situated at any of a plurality of x,y,z positions with respect to the front face of the grid template 740.

FIG. 1 also shows an x-y-z lock 120, shown as a wing-shaped feature, which functions similar to the flapper 1080 of the first embodiment. That is, the x-y-z lock can be rotated to a first position in order to release the hinges so as to allow freedom of movement of the targeting fixture 110, or it can be rotated to a second position in order to lock the hinges in place, at a desired x,y,z position of the medical instrument 700.

Figure 2:
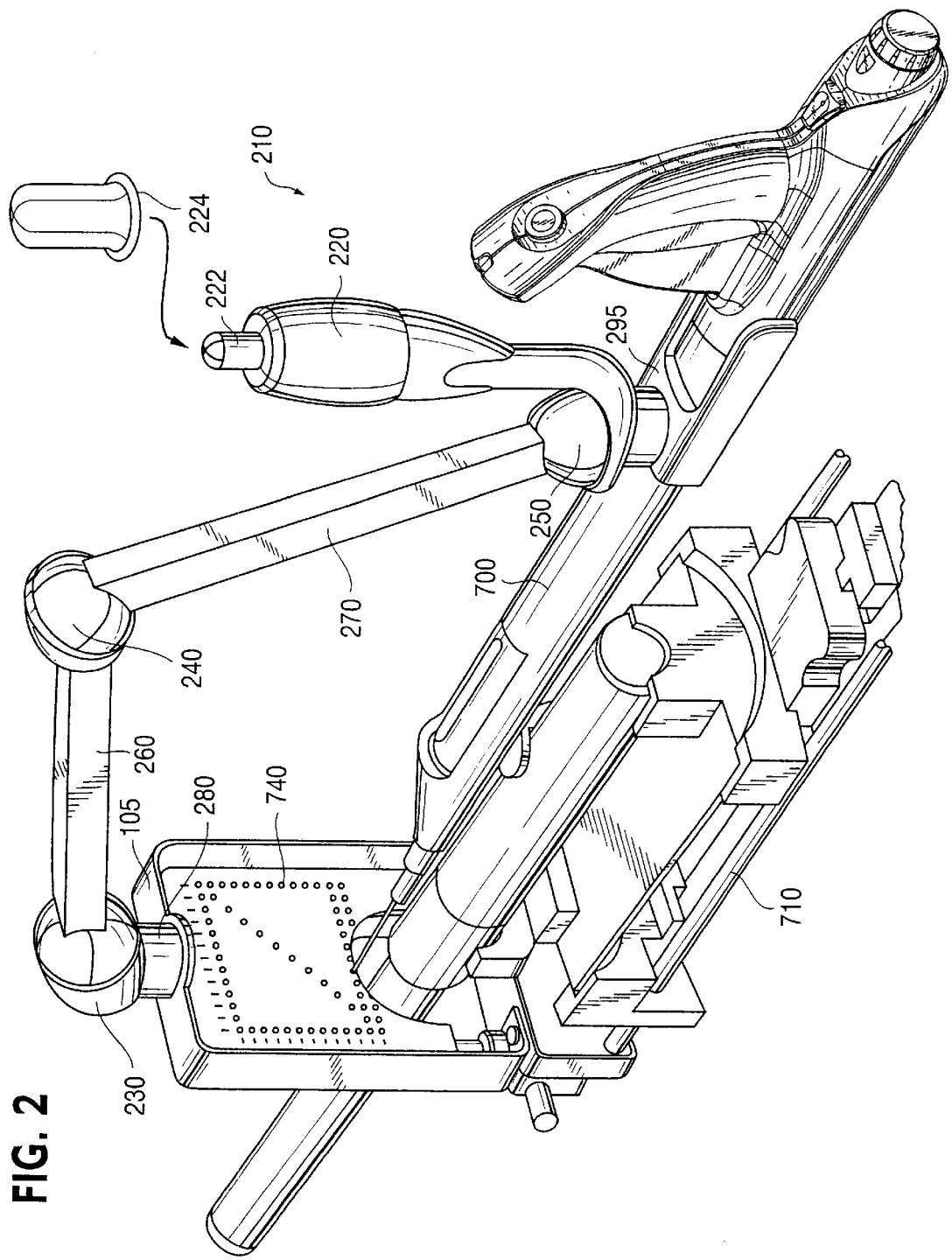
FIG. 2 shows a targeting fixture according to a third embodiment of the invention.

FIG. 2 shows a targeting fixture 210 according to a third embodiment of the invention. The targeting fixture 210 includes a first arm 280 that is rotatable with respect to a housing 105 surrounding the grid template 740. The first arm 280 is connected to a second arm 260 by a first ball-joint connection 230. The second arm 260 is connected at its other end to a third arm 270 by a second ball-joint connection 240. The third arm 250 is connected at its other end to a sheath unit 295 by way of a third ball-joint connection 250.

In FIG. 2, the boom release mechanism corresponds to a joystick 220 with a joystick button 222 at the top of the joystick 220. A sterile rubber part 224, can be placed on the joystick 220, in order to keep the device sterile. In the third embodiment, the joystick is kept at a locked position normally, and when the joystick button 222 is pushed, this action releases the tension on all of the ball joints, and then the targeting fixture 210 is free to move to a desired x,y,z position (with the joystick button 222 maintained in the down position). Once in place, the joystick button 222 is released, locking the targeting fixture 210 in place.

Figure 3:
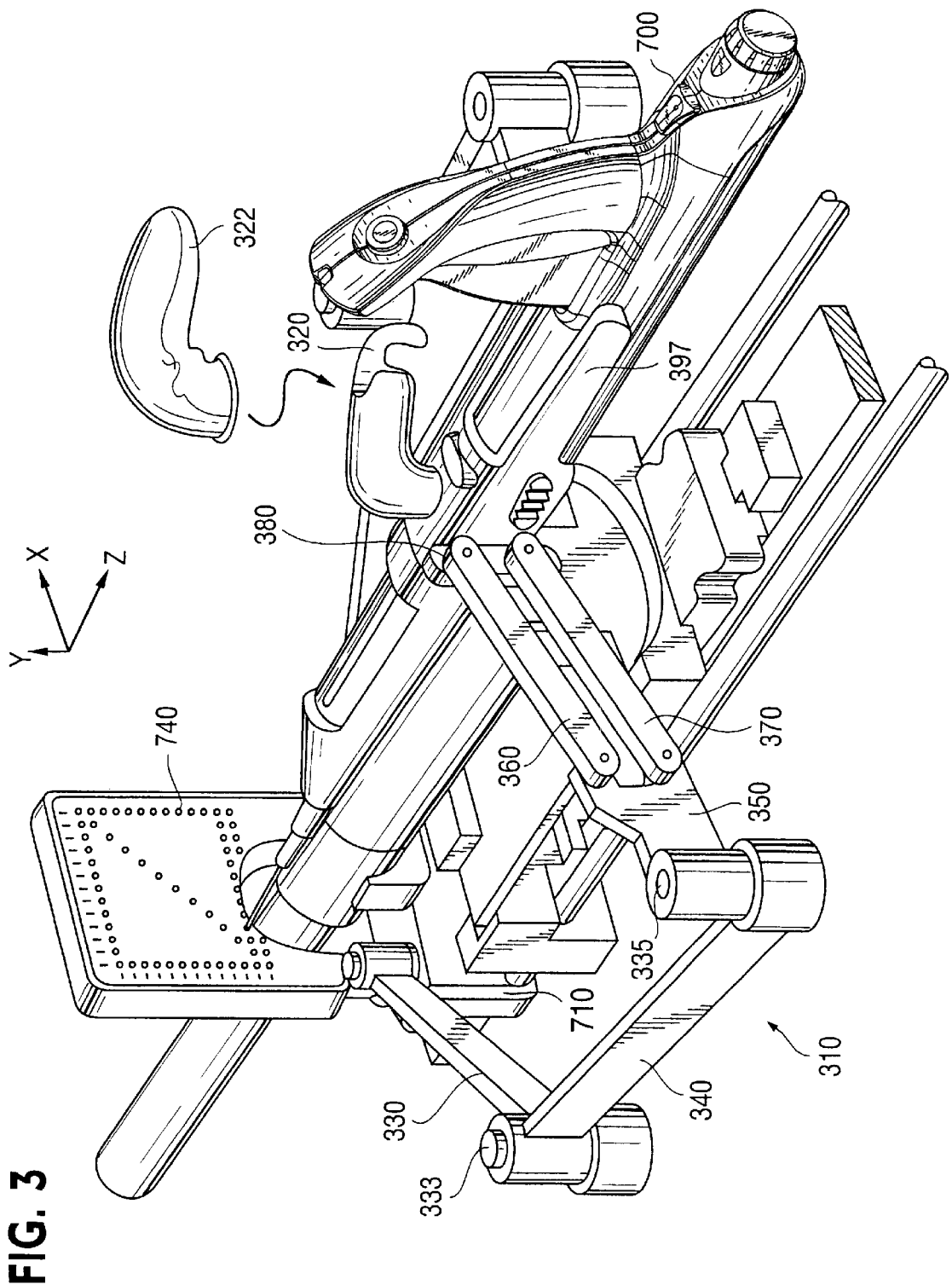
FIG. 3 shows a targeting fixture according to a fourth embodiment of the invention.

FIG. 3 shows a targeting fixture 310 according to a fourth embodiment of the invention. The targeting fixture 310 according to the fourth embodiment includes a first arm 330 that is pivotably attached to a portion of the base unit 710, on which the grid template 724 is also mounted thereon. A second arm 340 is pivotably attached to the first arm 330 by way of a first pivot point 333. A bracket piece 350 is pivotably attached to the other end of the second arm 340 by way of a second pivot point 335. The other end of the bracket piece 350 attaches to respective ends of two parallel parts 360, 370. The other ends of the two parallel parts 360, 370 are coupled to a part 380. The part 380 may be part of the sheath unit 397 that holds the medical instrument 700 in place, or it may couple to the sheath unit 397. A separate assembly on the opposite side of the medical instrument 700 is also partially shown in FIG. 3. Note, however, that only an assembly on one side is required, but a two-sided assembly is preferred. Not shown in FIG. 3 is a spring between the lower left side of the lower parallel arm 370, and the upper right side of the upper parallel arm 360. This diagonally-positioned springs provides a zero-balance feature for movement in the y-direction of the targeting fixture 310. The spring is of a force so as to counterbalance the weight of the sheath unit with the medical instrument provided thereon.

FIG. 3 also shows an index finger trigger 320, which is provided at a position such that while the operator is firing the medical instrument 700 by activating the trigger on the handle of the medical instrument 700 with his/her hand, the index finger on that same hand can be used to set/release the boom mechanism by way of the index finger trigger 320. When the index finger trigger 320 is not activated, the elements corresponding to the targeting fixture 310 are locked in place and cannot be moved, but when the index finger trigger 320 is activated, the targeting fixture 310 can be moved to placed the medical instrument 700 to a desired x,y,z position with respect to the grid template 740.

In an alternative configuration, the index finger trigger 320 can be placed on a slide on the top surface of the sheath unit 397, so that it is maintained close to the handle of the medical instrument 700 even while the medical instrument 700 is retracting with respect to the sheath unit 397 due to firing of seeds into a patient.

Figure 4:
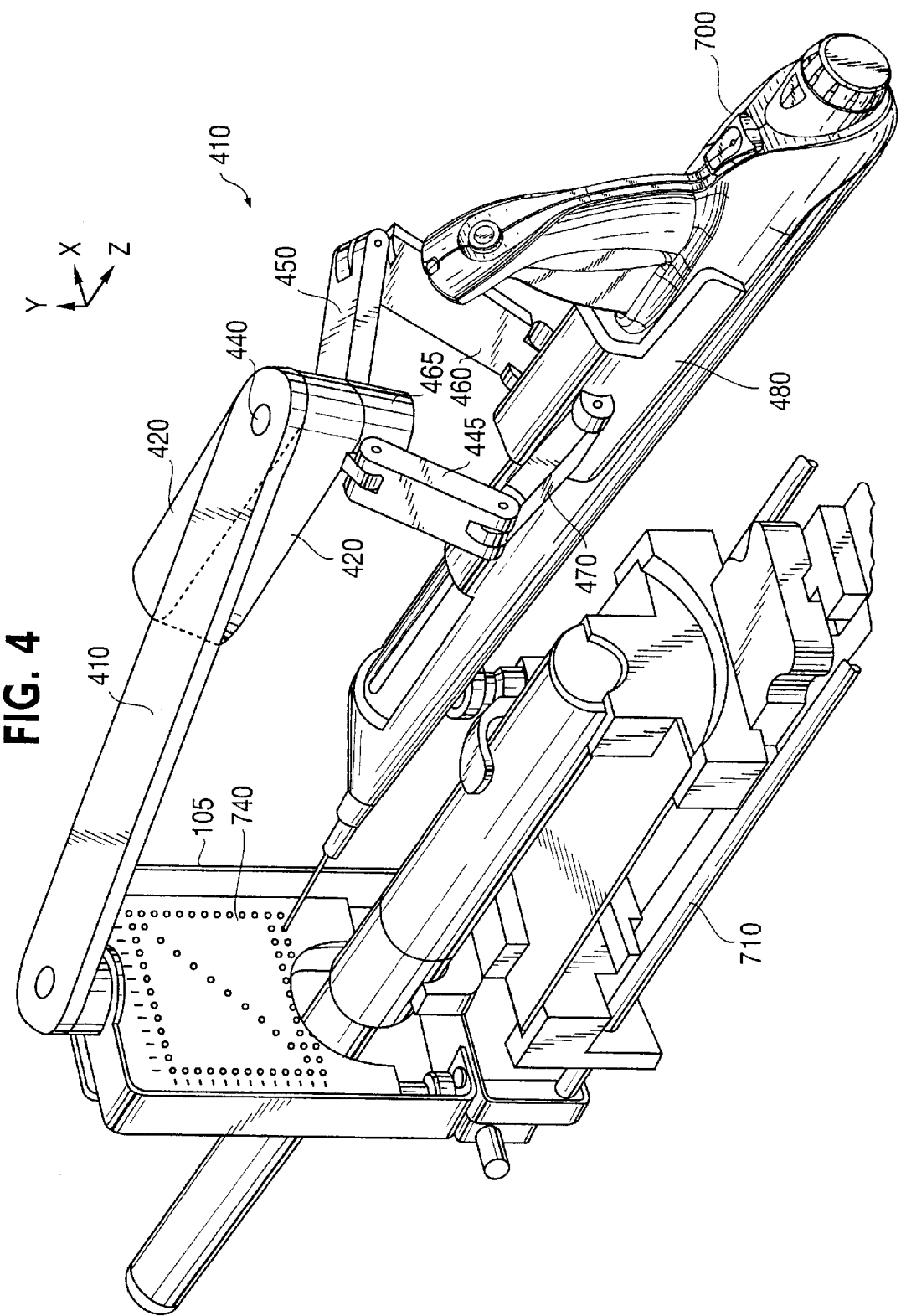
FIG. 4 shows a targeting fixture according to a fifth embodiment of the invention.

FIG. 4 shows a targeting fixture 410 according to a fifth embodiment of the invention. In the targeting fixture 410, a first arm 410 is pivotably attached to a housing 105 that surrounds the grid template 740. The first arm 410 is fixed in its y-position with respect to the grid template, and it moves along an arc with respect to the grid template 740. Two set of links, one set 445, 470 on the left side, and one set 450, 460 on the right side, are provided to allow y-axis movement of the sheath unit 480 with respect to the grid template 740. Thus, the first arm 410 and the two sets of links provide for x,y movement of the sheath unit 480 with respect to the grid template 740.

The targeting fixture 410 also includes a timing belt feature in order to maintain the longitudinal axis of the sheath unit 480 (and thus the medical instrument 700) orthogonal with respect to a plane corresponding to a front face of the grid template 740.

To provide the z-axis movement, the top links 445, 450 of the two sets of links are connected to the arm 410 via a cylindrical element 460, with an oval track unit 420 provided between the arm 410 and the cylindrical element 460. The oval track unit 420 remains parallel to the needle line, due to a timing belt provided between the oval track unit 420 and the arm 410. For example, a timing belt system similar to that described with respect to the first embodiment may be used. With the timing belt system in place, in order to maintain a precise relationship between the oval track unit 420 and the arm 410, the orthogonal positioning of the sheath unit 480 (and medical instrument 700) relative to the front face of the grid template is maintained.

The cylindrical element 450 extends out from a bottom surface of the oval track unit 420, and is shown in FIG. 4 as being positioned at the proximal end of the oval track unit 420. The cylindrical element 450 is capable of movement along a slot (not shown) provided on the bottom surface of the oval track unit 420, so as to be capable of movement from the proximal end to the distal end of the oval track unit 420. The cylindrical element 450 also is coupled with the respective top links 445, 450. This configuration allows for z-axis positioning of the sheath unit 480. Preferably, the length of the slot on the bottom surface of the oval track unit 420 is 3" or so, to cover a distance corresponding to a large prostate gland.

Figure 5:
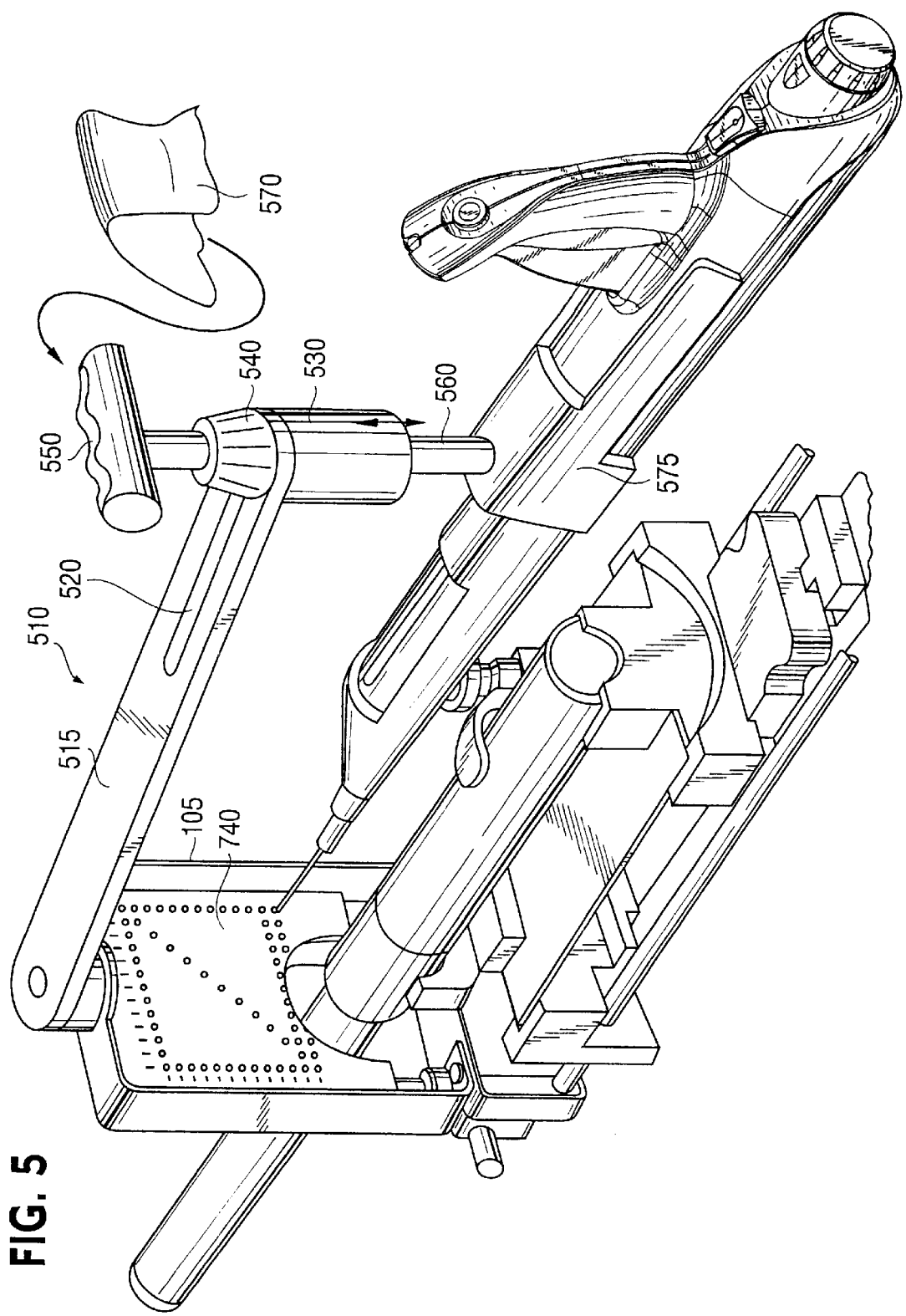
FIG. 5 shows a targeting fixture according to a sixth embodiment of the invention.

FIG. 5 shows a targeting fixture 510 according to a sixth embodiment of the invention. In the targeting fixture 510, a first arm 510 is pivotably attached to a housing 105 that surrounds the grid template 740. The first arm 510 is fixed in its y-position with respect to the grid template, and it moves along an arc with respect to the grid template 740. The other end of the first arm 510 is coupled to a y-axis movement assembly. The y-axis movement assembly includes a knob 550, on which a rubber piece 570 can be placed thereon to maintain sterility of the knob 550, if desired. The knob 550 is integral with a shaft 560. A nut 530 is rigidly provided on the shaft 560, directly below the first arm 515. A moveable nut 540 is provided on the shaft 560, directly above the first arm 515. When the knob 550 is turned in one direction, say clockwise, this loosens the moveable nut 540 to allow for up and down movement of the sheath unit 575 with respect to the first arm 515. Also provided in the targeting fixture 510 is a slot 520 on the first arm 515, whereby the entire y-axis assembly can be moved along the slot to desired z-axis position. Once the x,y,z position has been found, the targeting fixture 510 can be locked in place by turning the knob 550 in the other direction, thereby locking the moveable not 540 against the first arm 515. In this configuration, care must be taken so as not to move the first arm 515, since that arm is not locked into place by the knob 550. Preferably, the first arm 515 has some tension in its rotational movement, so that a somewhat strong amount of force is required to move it.

Figure 6:
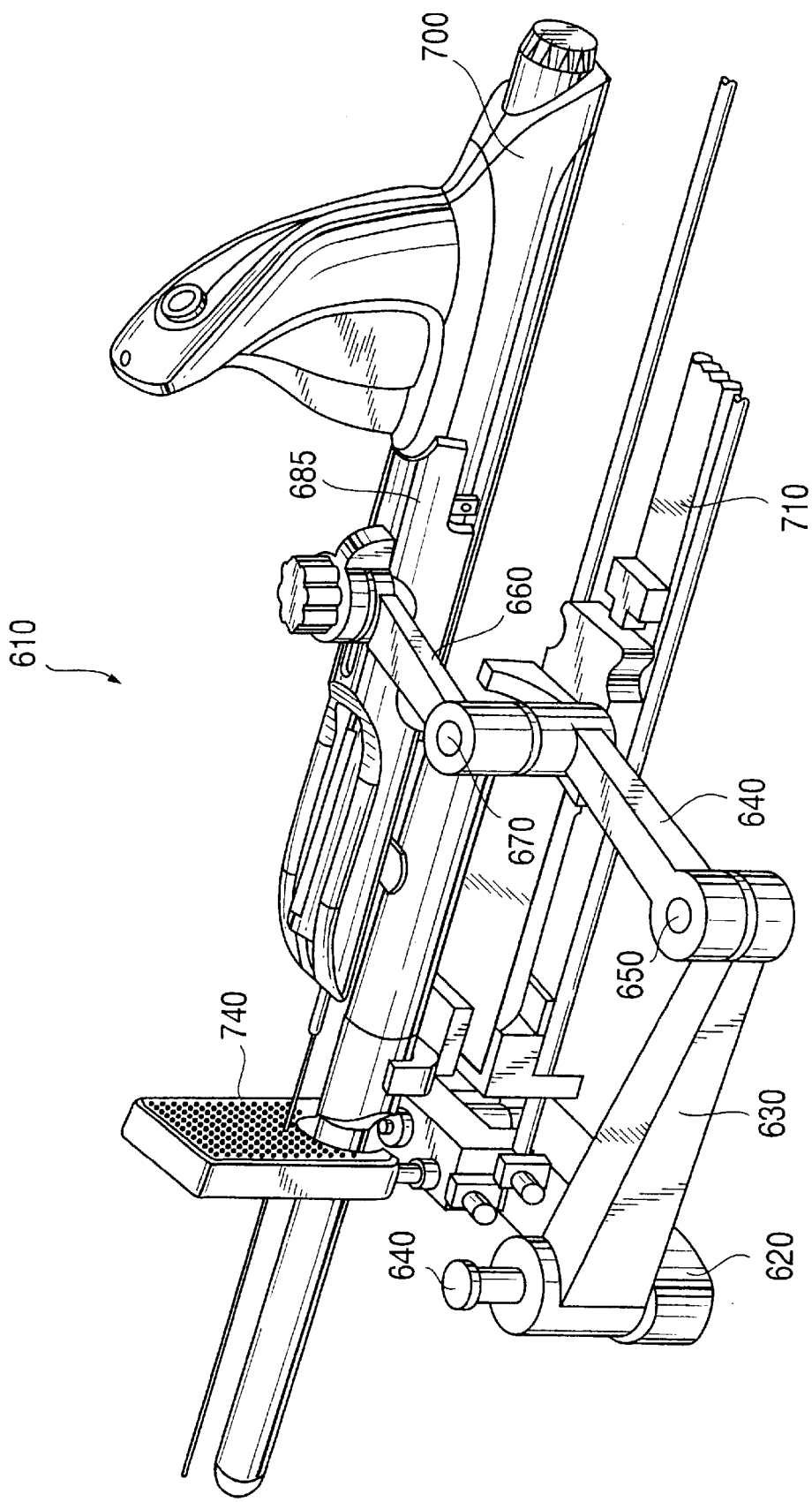
FIG. 6 shows a targeting fixture according to a seventh embodiment of the invention.

A seventh embodiment of a targeting fixture 610 is shown in FIG. 6. The targeting fixture 610 includes an attachment element 620, which attaches to the base unit 710 on which the grid template 740 is also attached to. A first arm 630 is attached to the attachment element 620, where the first arm 630 is rotatable with respect to the attachment element 620 and where the first arm 630 can be moved in a y-direction (up-down) with respect to the attachment element 620. The mechanism for providing such y-movement can be by way of a constant force spring as described in the first embodiment, or by other ways.

The other end of the first arm 630 is pivotably attached to a second arm 640, by way of pivot point 650. The second arm 640 is pivotably attached to a third arm 660 by way of pivot point 670. Like the first embodiment, the second and third arms 640, 660 preferably have respective timing belts in order to maintain the orthogonal nature of the longitudinal axis of the sheath unit 685 with respect to a plane corresponding to a front face of the grid template 740. Unlike the first embodiment, this embodiment does not provide a centralized location in which x,y,z movement can be locked in place, or released. Note that the y-axis movement can be performed at any of the pivot points 640, 650, 670 shown in FIG. 6.

An eighth embodiment of a targeting fixture 2110 is shown in FIGS. 21A and 21B. In the targeting fixture 2110, instead of using one arm and timing belts, it uses two parallel links. These parallel links are shown apart by some distance in FIGS. 21A and 21B for sake of clarity, but they may be disposed very close together in actuality. The locking screw 2120 is capable of locking out x,y,z motion simultaneously. An attachment bar 1230 couples to a sheath unit (not shown) in which a medical instrument 700 is provided therein.

Parallel links 2112 and 2114 are coupled to each other for common movement, by way of parallel links 2116 and 2118. Pivot points 2124, 2126, 2150, and 2140 couple these elements together. Pivot point 2124 is also connected to attachment bar 2130. Springs 2172 and 2174 are respectively provided at the top of the shafts that correspond to the pivot points 2140, 2150, and are provided to balance the weight of the targeting fixture 2110 (with the medical instrument 700 housed in the sheath unit of the targeting fixture 2110). This takes the place of the constant force spring of the computerized embodiment.

Parallel links 2142 and 2144 are coupled to the top part of the pivot points 2150, 2140, respectively, and can be locked in place by way of the locking screw 2120. By unlocking the locking screw 2120, the distal portion of the targeting fixture 2110 (see FIG. 21B) can be moved up or down with respect to the proximal portion of the targeting fixture 2110. Parallel links 2142 and 2144 are pivotably coupled to a ground plate 2180, by way of pivot points 2152 and 2154. The ground plate 2180 is a plate that is mounted onto the base unit 710 on which the grid template 740 is also mounted to.

While the above components are described with respect to the preferred embodiment, other similar types of components may be utilized, while remaining within the spirit and scope of the present invention, as exemplified by the claims. For example, the present invention is capable of coupling to different types of medical instruments, besides the one described that accepts a seed cartridge, since the only constraint is that the medical instrument has to be of a structure so as to fit within the sheath unit of the targeting fixture.

What is claimed is:

1. A targeting fixture for a grid template, comprising:

a sheath unit that is configured to receive a seed implanting device; and an x-y-z movement unit that provides x-, y- and z-direction movement of the sheath unit with respect to the grid template, wherein a longitudinal axis of the sheath unit is maintained in a fixed relationship with respect to a front face of the grid template.

2. The targeting fixture according to claim 1, wherein the fixed relationship is an orthogonal relationship.

3. The targeting fixture according to claim 1, further comprising a lock/unlock device that provides for locking and unlocking of the targeting fixture at one location on the targeting fixture.

* * * * *